US009309315B2

(12) United States Patent
Parren et al.

(10) Patent No.: US 9,309,315 B2
(45) Date of Patent: Apr. 12, 2016

(54) THERAPY WITH CD4 BINDING PEPTIDES AND RADIATION

(75) Inventors: Paul Parren, Odijk (NL); Ole Baadsgaard, Hellerup (DK); Denis Alexander, Cambridge (GB)

(73) Assignee: GENMAB A/S, Copenhagen (DK)

(*) Notice: Subject to any disclaimer, the term of this patent is extended or adjusted under 35 U.S.C. 154(b) by 1052 days.

(21) Appl. No.: 11/990,581

(22) PCT Filed: Aug. 18, 2006

(86) PCT No.: PCT/DK2006/000454
§ 371 (c)(1),
(2), (4) Date: Jan. 16, 2009

(87) PCT Pub. No.: WO2007/019865
PCT Pub. Date: Feb. 22, 2007

(65) Prior Publication Data
US 2010/0015134 A1    Jan. 21, 2010

Related U.S. Application Data

(60) Provisional application No. 60/709,943, filed on Aug. 18, 2005.

(51) Int. Cl.
A61K 39/395    (2006.01)
C07K 16/28    (2006.01)
A61K 31/37    (2006.01)
A61K 41/00    (2006.01)
A61K 39/00    (2006.01)

(52) U.S. Cl.
CPC ............. *C07K 16/2812* (2013.01); *A61K 31/37* (2013.01); *A61K 39/395* (2013.01); *A61K 41/0066* (2013.01); *A61K 2039/505* (2013.01)

(58) Field of Classification Search
None
See application file for complete search history.

(56) References Cited

U.S. PATENT DOCUMENTS

| | | | |
|---|---|---|---|
| 4,204,244 A | 5/1980 | Ho | |
| 5,175,384 A | 12/1992 | Krimpenfort et al. | |
| 5,204,244 A | 4/1993 | Fell et al. | |
| 5,434,340 A | 7/1995 | Krimpenfort et al. | |
| 5,530,101 A | 6/1996 | Queen et al. | |
| 5,690,933 A | 11/1997 | Cobbold et al. | |
| 5,770,429 A | 6/1998 | Lonberg et al. | |
| 5,859,205 A | 1/1999 | Adair et al. | |
| 6,511,665 B1 | 1/2003 | Dower et al. | |
| 7,084,260 B1 | 8/2006 | Lonberg et al. | |
| 7,722,873 B2 | 5/2010 | Lonberg et al. | |

FOREIGN PATENT DOCUMENTS

| | | |
|---|---|---|
| EP | 0315062 B1 | 5/1989 |
| EP | 0592106 A1 | 4/1994 |
| WO | 90/04036 A1 | 4/1990 |
| WO | 90/12878 A1 | 11/1990 |
| WO | 91/00906 A1 | 1/1991 |
| WO | 91/10741 A1 | 7/1991 |
| WO | 9201047 | 1/1992 |
| WO | 92/03918 A1 | 3/1992 |
| WO | 93/12227 A1 | 6/1993 |
| WO | 9311794 | 6/1993 |
| WO | 94/02602 A1 | 2/1994 |
| WO | 94/25585 A1 | 11/1994 |
| WO | 96/33735 A1 | 10/1996 |
| WO | 96/34096 A1 | 10/1996 |
| WO | 97/07671 A1 | 3/1997 |
| WO | WO-97/13852 A1 | 4/1997 |
| WO | 02/04021 A1 | 1/2002 |

OTHER PUBLICATIONS

Kon et al , The Lancet 352:1109, 1998.*
Burgess et al, Journal of Cell biology, 111:p. 2129-2138, 1990.*
Knox et al, Blood 77:20-30, 1991.*
Lundin et al, Current Tr Op Onco, 5:203-214, 2004.*
Veillette et al, Nature 338:257-259, 1989.*
Mestel et al, Expert Opin. Biol Ther. 8:1929-1939, 2008.*
Clinical trials, Aug. 8, 2003-2005.*
DocGuide.com, Web publication, May 2004.*
L. Musajo (Pure Apple. Chem, 6:369-384, 1963.*
Ivie, J Agri Food Chem 26:1394-1403,1978.*
Rupoli e tal, Haematologica 84:809-813, 1999.*
Hagberg et al Medical Oncolog 22:191-194, 2005.*
Skov et al, Arch Dermatol 139:1433-9, 2003, abstract only.*
Fishwild et al, Clin Immu 92:138-139, 1999.*
Morel, Patricia et al., "Anti-CD4 Monoclonal Antibody Therapy in Severe Psoriasis," Journal of Autoimmunity, vol. 5:465-477 (1992).
Baron, Elma D. et al., "Phototherapy for cutaneous T-cell lymphoma," *Dermatologic Therapy*, vol. 16:303-310 (2003).
Böhnke, A. et al., "Role of p53 mutations, protein function and DNA damage for the radiosensitivity of human tumour cells," *Int. J. Radiat. Biol.*, vol. 80(1):53-63 (2004).
Bruyns, Catherine et al., "The Two SH2-Domain-Containing Inositol 5-Phosphatases SHIP1 and SHIP2 Are Coexpressed in Human T Lymphocytes," *Biol. Chem.*, vol. 380:969-974 (1999).
Cuddihy, Andrew R. et al., "The p53 protein family and radiation sensitivity: Yes or no?," *Cancer and Metastasis*, vol. 23:237-257 (2004).
Genmab A/S, "Genmab Obtains Special Protocol Assessment Agreement for Humax-CD4™ Pivotal Study," Press Release (2005).
Genmab A/S, "Genmab Regains Rights to Humax-CD4," Press Release (2007).

(Continued)

*Primary Examiner* — Lei Yao
(74) *Attorney, Agent, or Firm* — Nelson Mullins Riley & Scarborough LLP; Jane E. Remillard, Esq.; Christopher L. Frank

(57) ABSTRACT

The present invention relates to a peptide, such as an antibody, capable of binding to CD4 and use thereof for the mediation of radiation treatment of a clinical condition. The radiation treatment may for instance by treatment with PUVA.

34 Claims, 5 Drawing Sheets

(56) References Cited

OTHER PUBLICATIONS

Grandage, V.L. et al., "PI3-kinase/Akt is constitutively active in primary acute myeloid leukaemia cells and regulates survival and chemoresistance via NF-$_\kappa$B, MAPkinase and p53 pathways," *Leukemia*, vol. 19:286-594 (2005).

Hashimoto, Yoshio et al., "Flow cytometric analysis of pig epidermal keratinocytes: effects of ultraviolet B irradiation (UVB) and topical PUVA treatment," *Journal of Dermatological Science*, vol. 10:16-24 (1995).

Havenith, C.E. et al., "HuMax-CD4, a fully human monoclonal antibody: Mechanisms of actions and early results in cutaneous T-cell lymphoma," *Immunobiology*, vol. 209:360, No. G.9 (2004).

Horn, S. et al., "Restoration of Ship activity in a human leukemia cell line downregulates constitutively activated phosphatidylinositol 3-kinase/Akt/GSK-3β signaling and leads to an increased transit time through the G1 phase of the cell cycle," *Leukemia*, vol. 18:1839-1849 (2004).

Huang, Shyh-Min et al., "Modulation of Radiation Response after Epidermal Growth Factor Receptor Blockade in Squamous Cell Carcinomas: Inhibition of Damage Repair, Cell Cycle Kinetics, and Tumor Angiogenesis," *Clinical Cancer Research*, vol. 6:2166-2174 (2000).

Johnson, Ray et al., "PUVA Treatment Selectively Induces a Cell Cycle Block and Subsequent Apoptosis in Human T-Lymphocytes," *Photochemistry and Photobiology*, vol. 63(5):566-571 (1996).

Kacinski, Barry M. et al., "Apoptosis and Cutaneous T Cell Lymphoma," *Ann. N. Y. Acad. Sci.*, vol. 941:194-199 (2001).

Lamkin, Thomas D. et al., "She Interaction with Src Homology 2 Domain Containing Inositol Phosphatase (SHIP) in Vivo Requires the Shc-PHosphotyrosine Binding Domain and Two Specific Phosphotyrosines on SHIP," *The Journal of Biological Chemistry*, vol. 272(16):10396-10401 (1997).

Ma, W. et al., "Long-term growth arrest of PUVA-treated fibroblasts in G2/M in the absence of p16$^{INK4a}$, p21$^{CIP1}$ or p53," *Experimental Dermatology*, vol. 12:629-637 (2003).

Martelli, Maria Paola et al., "T Cell Regulation of p62dok (Dok1) Association with Crk-L," *The Journal of Biological Chemistry*, vol. 276(49):45654-45661 (2001).

McIlwrath, Amanda J. et al., "Cell Cycle Arrests and Radiosensitivity of Human Tumor Cell Lines: Dependence on Wild-Type p53 for Radiosensitivity," *Cancer Research*, vol. 54:3718-3722 (1994).

Nagasawa, Masayuki et al., "Accumulation of high levels of the p53 and p130 growth-suppressing proteins in cell lines stably over-expressing cyclin-dependent kinase 6 (cdk6)," *Oncogene*, vol. 20:2889-2899 (2001).

Ng, C.E. et al., "Characterization of radiation sensitivity of human squamous carcinoma A431 cells," *Br. J. Cancer*, vol. 56:301-307 (1987).

Okabe, Seiichi et al., "Stromal cell-derived factor-1α/CXCL12-induced chemotaxis of T cells involves activation of the RasGAP-associated docking protein p62Dok-1," *Blood*, vol. 105(2):474-480 (2005).

Okkenhaug, Klaus et al., "PI3K in Lymphocyte Development, Differentiation and Activation," *Nature Reviews Immunology*, vol. 3:317-330 (2003).

Rider, David A. et al., "A Human CD4 Monoclonal Antibody for the Treatment of T-Cell Lymphoma Combines Inhibition of T-Cell Signaling by a Dual Mechanism with Potent Fc-Dependent Effector Activity," *Cancer Res.*, vol. 67(20):9945-9953 (2007).

Takemura, T. et al., "Role of G1 phase in the UV-induced apoptosis of EL-4 mouse lymphoma cells," *Apoptosis*, vol. 4:245-253 (1999).

Taylor, Vanessa et al., "5' Phospholipid Phosphatase SHIP-2 Causes Protein Kinase B Inactivation and Cell Cycle Arrest in Glioblastoma Cells," *Molecular and Cellular Biology*, vol. 20(18):6860-6871 (2000).

Veillette, André et al., "Negative Regulation of Immunoreceptor Signaling," *Annu. Rev. Immunol.*, vol. 20:669-707 (2002).

Veillette, André et al., "The CD4 and CD8 T Cell Surface Antigens Are Associated with the Internal Membrane Tyrosine-Protein Kinase p56$^{lck}$," *Cell*, vol. 55:301-308 (1988).

Yamakawa, Norio et al., "The rasGAP-binding protein, Dok-1, mediates activin signaling via serine/threonine kinase receptors," *The EMBO Journal*, vol. 21(7):1684-1694 (2002).

Bethea, Deidra et al., "Psoralen photobiology and photochemotherapy: 50 years of science and medicine," *Journal of Dermatological Science*, vol. 19:78-88 (1999).

Havenith, C.E. et al., "HuMax-CD4, a fully human monoclonal antibody: Mechanisms of actions and early results in cutaneous T-cell lymphoma," *Joint Annual Meeting of the German and Dutch Societies for Immunology (JAMI), Immunobiology*, vol. 209:360 (2004).

Kim, Y.H. et al., "HuMax-CD4 fully human monoclonal antibody: phase II trial in cutaneous T cell lymphoma," *The Journal of Investigative Dermatology*, vol. 122(3):A57, Abstract No. 342 (2004).

Konstantinow, Alexander et al., "Treatment of cutaneous T-cell lymphoma with extracorporeal photochemotherapy," *Journal of the European Academy of Dermatology and Venereology*, vol. 9:111-117 (1997).

Skov, Lone et at, "A Fully Human Monoclonal Anti-CD4 Antibody for the Treatment of Psoriasis Vulgaris," *Arch. Dermatol.*, vol. 139:1433-1439 (2003).

International Search Report for Application No. PCT/DK2006/000454, dated Mar. 20, 2007.

Alt, Frederick W. et al., "Immunoglobulin genes in transgenic mice," *Trends in Genetics*, vol. 1:231-236 (1985).

Berman, Jeffrey E. et al., "Content and organization of the human Ig VH locus: definition of three new VH families and linkage to the Ig CH locus," *The EMBO J.*, vol. 7:727-738 (1988).

Berton, Michael T. et al., "Synthesis of germ-line g1 immunoglobulin heavy-chain transcripts in resting B cells: Induction by interleukin 4 and inhibition by interferon g," *Proc. Natl. Acad. Sci. (U.S.A.)*, vol. 86:2829-2833 (1989).

Bollag, Roni J. et al, "Homologous recombination in mammalian cells," *Annu. Rev. Genet.*, vol. 23:199-225 (1989).

Bose, Biplab et al., "Problems in using statistical analysis of replacement and silent mutations in antibody genes for determining antigen-driven affinity selection," *Immunology*, vol. 116:172-183 (2005).

Bruggemann, Marianne et al., "A repertoire of monoclonal antibodies with human heavy chains from transgenic mice," *Proc. Natl. Acad. Sci. USA*, vol. 86:6709-6713 (1989).

Bruggemann, Marianne et al., "Human antibody production in transgenic mice: expression from 100 kb of the human IgH locus," *Eur. J. Immunol.*, vol. 21:1323-1326 (1991).

Bucchini, D. et al, "Rearrangement of a chicken immunoglobulin gene occurs in teh lymphoid lineage of transgenic mice," *Nature*, vol. 326:409-411 (1987).

Buttin, G., "Exogenous Ig gene rearrangement in transgenic mice: a new strategy for human monoclonal antibody production?" *TIG*, vol. 3(8):205-206 (1987).

Capecchi, Mario R., "Altering the genome by homologous recombination," *Science*, vol. 244:1288-1292 (1989).

Capecchi, Mario R., "The new mouse genetics: Altering the genome by gene targeting," *TIG*, vol. 5:70-76 (1989).

Chen, Pojen P. et al., "Characterization of Two Immunoglobulin VH Genesz that are Homologous to Human Rheumatoid Factors," *Arthritis Rheum.*, vol. 32(1):72-76 (1989).

Chien, Nadine C. et al., "Significant structural and functional change of an antigen-binding site by a distant amino acid substitution: Proposal of a structural mechanism," *Proc. Natl. Acad. Sci. USA*, vol. 86:5532-5536 (1989).

Coffman, Robert L. et al., "A mouse T cell product that preferentially enhances IgA production," *J. Immunol.*, vol. 139:3685-3690 (1987).

Coffman, Robert L. et al., "A T cell activity that enhances polyclonal IgE production and its inhibition by interferon-g," *J. Immunol.*, vol. 136:949-954 (1986).

Doetschman, Thomas et al., "Targetted correction of a mutant HPRT gene in mouse embryonic stem cells," *Nature*, vol. 330:576-578 (1987).

Durdik, Jeannine et al., "Isotype switching by a microinjected m immunoglobulin heavy chain gene in transgenic mice," *Proc. Natl. Acad. Sci. USA*, vol. 86:2346-2350 (1989).

Esser, Charlotte et al., "Rapid induction of transcription of unrearranged Sg1 switch regions in activated murine B cells by interleukin 4," *The EMBO J.*, vol. 8:483-488 (1989).

(56) References Cited

OTHER PUBLICATIONS

Ferrier, Pierre et al., "Separate elements control DJ adn VDJ rearrangement in a transgenic recombination substrate," The EMBO J., vol. 9:117-125 (1990).
Fishwild, Dianne M. et al., "High-Avidity human IgGk monoclonal antibodies from a novel strain of minilocus transgenic mice," Nature Biotechnology, vol. 14:845-851 (1996).
Forni, Luciana et al., "Extensive splenic B cell activation in IgM-transgenic mice," Eur. J. Immunol., vol. 20:983-989 (1990).
Gerstein, Rachel M. et al., "Isotype switching of an immunoglobulin heavy chain transgene occurs by DNA recombination between different chromosomes," Cell, vol. 63:537-548 (1990).
Goodhardt, M. et al., "Rearrangement and expression of rabbit immunoglobulin k light chain gene in transgenic mice," Proc. Natl. Acad. Sci. (U.S.A.), vol. 84:4229-4233 (1987).
Gordon, Jon W., "Transgenic mice in immunology," The Mount Sinai Journal of Medicine, vol. 53:223-231 (1986).
Green, L.L., et al., "Antigen-specific human monoclonal antibodies from mice engineered with human Ig heavy and light chain YACs," Nature Genetics, vol. 7:13-21 (1994).
Hagman, James et al., "Inhibition of immunoglobulin gene rearrangement by the expression of a I2 transgene," J. Exp. Med., vol. 169:1911-1929 (1989).
Heike, Michael et al., "Specificities and Functions of CD4+ HLA Class II-Restricted T Cell Clones Against a Human Sarcoma," The Journal of Immunology, vol. 156:2205-2213 (1996).
Hofker, Marten H. et al., "Complete physical map of the human immunoglobulin heavy chain constant region gene complex," Proc. Natl. Acad. Sci. USA, vol. 86:5567-5571 (1989).
Humphries, C.G. et al., "A new human immunoglobulin VH family preferentially rearranged in immature B-cell tumours," Nature, vol. 331:446-449 (1988).
Ichihara, Y. et al., "Organization of human immunoglobulin heavy chain diversity gene loci," The EMBO J., vol. 7:4141-4150 (1988).
Iglesias, Antonio et al., "Expression of immunoglobulin delta chain causes allelic exclusion in transgenic mice," Nature, vol. 330:482-484 (1987).
Jaenisch, Rudolf, "Transgenic Animals," Science, vol. 240:1468-1474 (1988).
Jakobovits, Aya et al., "Analysis of homozygous mutant chimeric mice: Deletion of the immunoglobulin heavy-chain joining region blocks of B-cell development and antibody production," Proc. Natl. Acad. Sci. USA, vol. 90:2551-2555 (1993).
Jakobovits, Aya et al., "Production of Antigen-Specific Human Antibodies from Mice Engineered with Human Heavy and Light Chain Yacs," Annals of the New York Academy of Sciences, vol. 764:525-535 (1995).
James, Keith et al., "Human monoclonal antibody production current status and future prospects," J. of Immunol. Methods, vol. 100:5-40 (1987).
Janeway, Charles A. Jr. et al, Immunobiology, 3rd Edition, Garland Publishing Inc., New York, pp. 3:31 and 3:21 (1997).
Janeway, Charles A. Jr. et al, Immunobiology, 5th Edition, Garland Publishing, New York, pp. 94-105 (2001).
Jasin, Maria et al., "Homologous integration in mammalian cells without target gene selection," Genes & Development, vol. 2:1353-1363 (1988).
Jonker, M. et al., "In Vivo Treatment with a Monoclonal Chimeric Anti-CD4 Antibody Results in Prolonged Depletion of Circulating CD4+ Cells in Chimpanzees," Clin. Exp. Immunol., vol. 93:301-307 (1993).
Jung, Steffen et al., "Shutdown of class switching recombination by deletion of a switch region control element," Science, vol. 259:984-987 (1993).
Kenny, James J. et al., "Alteration of the B cell surface phenotype, immune response to phosphocholine and the B cell repertoire in M167 a plus k transgenic mice," J. of Immunol., vol. 142:4466-4474 (1989).
Kitamura, Daisuke et al., "A B cell-deficient mouse by targeted disruption of the membrane exon of the immunoglobulin m chain gene," Nature, vol. 350:423-426 (1991).
Koller, Beverly H. et al., "Inactivating the b2-microglobulin locus in mouse embryonic stem cells by homologous recombination," Proc. Natl. Acad. Sci. USA, vol. 86:8932-8935 (1989).
Lin, F.-L. et al., "Recombination in mouse L cells between DNA introduced into cells and homologous chromosomal sequences," Proc. Natl. Acad. Sci. USA, vol. 82:1391-1395 (1985).
Linton, Phyllis-Jean et al., "Primary antibody-forming cells secondary B cells are generated from separate precursor cell subpopulations," Cell, vol. 59:1049-1059 (1989).
Lo, David et al., "Expression of mouse IgA by transgenic mice, pigs and sheep," Eur. J. Immunol., vol. 21:1001-1006 (1991).
Lonberg, Nils et al., "Antigen-specific human antibodies from mice comprising four distinct genetic modifications," Nature, vol. 368:856-859 (1994).
Lonberg, Nils et al., "Human Antibodies from Transgenic Mice," International Reviews of Immunology, Harwood Academic Publishers, London, vol. 13:65-93, (1995).
Lorenz, Wulfing et al., "Physical map of the human immunoglobulin k locus and its implications for the mechanisms of Vk-Jk rearrangement," Nucl. Acids Res., vol. 15:9667-9676 (1987).
Lorincz, Allan L., "Cutaneous T-cell lymphoma (mycosis fungoides)," The Lancet, vol. 347:871-876 (1996).
Lutzker, Stuart et al., "Structure and expression of germ line immunoglobulin g2b transcripts," Mol. Cell Biol., vol. 8:1849-1852 (1988).
Mansour, Suzanne L. et al., "Disruption of the proto-oncogene int-2 in mouse embryo-derived stem cells: a general strategy for targeting mutations to non-selectable genes," Nature, vol. 336:348-352 (1988).
Matutes, E. et al., "Clinical and Laboratory Features of 78 Cases of T-Prolymphocytic Leukemia," Blood, vol. 78 (12):3269-3274 (1991).
Merkenschlager, Matthias et al., "Functional Epitope Analysis of the Human CD4 Molecule, The MHC Class II-Dependent Activation of Resting T Cells Is Inhibited by Monoclonal Antibodies to CD4 Regardless whether or Not They Recognize Epitopes Involved in the Binding of MHC Class II or HIV gp120," The Journal of Immunology, vol. 145 (9):2839-2845 (1990).
Miller, Jim et al., "Structural alterations in J regions of mouse immunoglobulin I genes are associated with differential gene expression," Nature, vol. 295:428-430 (1982).
Mills, Frederick C. et al., "DNase I hypersensitive sites in the chromatin of human m immunoglobulin heavy-chain genes," Nature, vol. 306:809-812 (1983).
Mills, Frederick C. et al., "Sequences of human immunoglobulin switch regions: implications for recombination and transcription," Nucl. Acids. Res., vol. 18:7305-7316 (1991).
Morrison, Sherie L., "Success in specification," Nature, vol. 368:812-813 (1994).
Mowatt, Michael R. et al., "DNA sequence of the murine g1 switch segment reveals novel structural elements," J. Immunol., vol. 136:2674-2683 (1986).
Muller, Werner et al., "Membrane-bound IgM Obstructs B cell development in transgenic mice," Eur. J. Immunol., vol. 19:923-928 (1989).
Murray, Andrew W. et al., "Construction of artificial chromosomes in yeast," Nature, vol. 305:189-193 (1983).
Neuberger, Michael, "Generating high-avidity human mabs in mice," Nature Biotechnology, vol. 14:826 (1996).
Neuberger, Michael et al, "Isotype exclusion and transgene down-regulation in immunoglobulin-I transgenic mice," Nature, vol. 338:350-352 (1989).
Newman, Roland et al., "'Primatization' of Recombinant Antibodies for Immunotherapy of Human Diseases: A Macaque/Human Chimeric Antibody Against Human CD4," Biotechnology, vol. 10(11):1455-1460 (1992).
Nikaido, Toshio et al., "Nucleotide sequences of switch regions of immunoglobulin C and C genes and their comparison," J. Biol. Chem., vol. 257:7322-7329 (1982).

(56) References Cited

OTHER PUBLICATIONS

Nikaido, Toshio et al., "Switch region of immunoglobulin Cm gene is composed of simple tandem repetitive sequences," Nature, vol. 292:845-848 (1981).
Nussenzweig, Michel C. et al., "A human immunoglobulin gene reduces the incidence of lymphomas in C-Myc-bearing transgenic mice," Nature, vol. 336:446-450 (1988).
Nussenzweig, Michel C. et al., "Allelic exclusion in transgenic mice carrying mutant human IgM genes," J. Exp. Med., vol. 167:1969-1974 (1988).
Oettinger, Marjorie A. et al., "RAG-1 and RAG-2, adjacent genes that synergistically activates V(D)J recombination," Science, vol. 248:1517-1523 (1990).
Padlan, Eduardo A., "Anatomy of the Antibody Molecule," Molecular Immunology, vol. 31(3):169-217 (1994).
Petters, R.M., "Transgenic mice in immunological research," Vet. Immunol. Immunopath., vol. 17:267-278 (1987).
Pettersson, Sven et al., "A second B cell-specific enhancer 3' of the immunoglobulin heavy-chain locus," Nature, vol. 344:165-168 (1990).
Portolano, Stefano et al., "Lack of Promiscuity in Autoantigen-Specific H and L Chain Combinations as Revealed by Human H and L Chain 'Roulette'," The Journal of Immunology, vol. 150(3):880-887 (1993).
Powelson, John A. et al., "CDR-Grafted OKT4A Monoclonal Antibody in Cynomolgus Renal Allograft Recipients," Transplantation, vol. 57(6):788-793 (1994).
Rabbitts, T.H. et al., "Human immunoglobulin heavy chain genes: evolutionary comparisons of Cm, Cd and Cg genes and associated switch sequences," Nucl. Acids Res., vol. 9:4509-4524 (1981).
Rath, Satyajit et al., "B cell abnormalities induced by a m lg transgene extend to L chain isotype usage," J. of Immunol., vol. 146(8):2841-2846 (1991).
Rath, Satyajit et al., "Quantitative analysis of idiotypic mimicry and allelic exclusion in mice with a m lg Transgene," J. of Immunol., vol. 143:2074-2080 (1989.
Ravetch, J.V. et al., "Evolutionary approach to the question of immunoglobulin heavy chain switching: Evidence from cloned human and mouse genes," Proc. Natl. Acad. Sci. (U.S.A>), vol. 77:6734-6738 (1980).
Reid, Laurence E. et al., "A single DNA response element can confer inducibility by both a- and g-interferons," Proc. Natl. Acad. Sci. (U.S.A.), vol. 86:840-844 (1989).
Ritchie, Kindred A. et al., "Allelic exclusion and control of endogenous immunoglobulin gene rearrangement in k transgenic mice," Nature, vol. 312:517-520 (1984).
Rothman, Paul et al. "Structure and expression of germline immunoglobulin g3 heavy chain gene transcripts: implications for mitogen and lymphokine directed class-switching," Intl. Immunol., vol. 2:621-627 (1990).
Rudikoff, Stuart et al., "Single amino acid substitution altering antigen-binding specificity," Proc. Natl. Acad. Sci. USA, vol. 79:1979-1983 (1982).
Rusconi, Sandro et al., "Transmission and expression of a specific pair of rearranged immunoglobulin m and k genes in a transgenic mouse line," Nature, vol. 314:330-334 (1985).
Sahin, Ugur et al., "Human neoplasms elicit multiple specific immune responses in the autologous host," Proc. Natl. Acad. Sci. USA, vol. 92:11810-11813 (1995).
Sato, Takayuki et al., "Physical linkage of a variable region segment and the joining region segment of the human immunoglobulin heavy chain locus," Biochem. Biophys. Res. Comm., vol. 154:264-271 (1988).
Scangos, George et al., "Gene transfer into mice," Advances in Genetics, vol. 24:285-322 (1987).
Sedivy, John M. et al., "Positive genetic selection for gene disruption in mammalian cells by homologous recombination," Proc. Natl. Acad. Sci. USA, vol. 86:227-231 (1989).
Shimizu et al, "Immunoglobulin double-isotype expression by trans-mRNA in a human immunoglobulin transgenic mouse," Proc. Natl. Acad. Sci. USA, vol. 86:8020-8023 (1989).
Shimizu et al, "Trans-splicing as a possible molecular mechanism for the multiple isotype expression of the immunoglobulin gene," J. Exp. Med., vol. 173:1385-1393 (1991).
Sideras et al, "Production of sterile transcription of Cg genes in an IgM-producing human neoplastic B cell line that switches to IgG-producing cells," Intl. Immunol., vol. 1:631-642 (1989).
Siebenlist et al, "Human immunoglobulin D segments encoded in tandem multigenic families," Nature, vol. 294:631-635 (1981).
Silberstein, L.E. et al, "Variable Region Gene Analysis of Pathologic Human Autoantibodies to teh Related i and I Red Blood Cells Antigens," Blood, vol. 78(9):2372-2386 (1991).
Smithies et al, "Insertion of DNA sequences into the human chromosomal b-globulin locus by homologous recombination," Nature, vol. 317:230-234 (1985).
Snapper et al, "Interferon-gamma and B cell stimulatory factor-1 reciprocally regulate lg isotype production," Science, vol. 236:944-947 (1987).
Song et al, "Accurate modification of a chromosomal plasmid by homologous recombination in human cells," Proc. Natl. Acad. Sci. USA, vol. 84:6820-6824 (1987).
Soriano et al, "Targeted disruption of the c-src proto-oncogene leads to osteopetrosis in mice," Cell, vol. 64:693-702 (1991).
Stavnezer et al, "Immunoglobulin heavy-chain switching may be directed by prior induction of transcripts from constant-region genes," Proc. Natl. Acad. Sci. (U.S.A.), vol. 85:7704-7708 (1988).
Stites et al, Basic & Clinical Immunology, p. 50 (1984).
Storb et al, "Expression, allelic exclusion and somatic mutation of mouse immunoglobulin kappa genes," Immunological Reviews, vol. 89:85-102 (1986).
Storb, "Immunoglobulin gene analysis in transgenic mice," Immunoglobulin Genes, Academic Press Limited, pp. 303-326 (1989).
Szurek et al, "Complete nucleotide sequence of the murine g3 switch region and analysis of switch recombination in two g3-expressing hybridomas," J. Immunol., vol. 135:620-626 (1985).
Tahara et al, "HLA antibody responses in HLA class I transgenic mice," Immunogenetics, vol. 32:351-360 (1990).
Takeda, Isao et al., "Analysis of Tissue Lymphocytes by Double Fluorescent Staining Gastric Cancer Tissue and Regional Lymph Nodes," Japanese Journal of Surgery, vol. 17(3):156-161 (1987).
Taki et al, "Targeted insertion of a variable region gene into the immunoglobulin heavy chain locus," Science, vol. 262:1268-1271 (1993).
Tanaka et al, "An antisense oligonucleotide complementary to a sequence in Ig2b increases g2b germline transcripts, stimulates B cell DNA synthesis, and inhibits immunoglobulin secretion," The Journal of Experimental Medicine, vol. 175:597-607 (1992).
Taussig et al, "Regulation of immunoglobulin gene rearrangement and expression," Immunology Today, vol. 10:143-146 (1989).
Taylor et al, "Human immunoglobulin transgenes undergo rearrangement, somatic mutation and class switching in mice that lack endogenous IgM," International Immunology, vol. 6:579-591 (1994).
Taylor, L.D. et al, "A Transgenic Mouse that Expresses a Diversity of Human Sequence Heavy and Light Chain Immunoglobulins," Nucleic Acids Research, vol. 20(23):6287-6295 (1992).
Thomas and Capecchi, "Site-directed mutagenesis by gene targeting in mouse embryo-derived stem cells," Cell, vol. 51:503-512 (1987).
Thomas et al, "High frequency targeting of genes to specific sites in the mammalian genome," Cell, vol. 44:419-428 (1986).
Tomlinson et al, "The Repertoire of Human Germline VH Sequences Reveals About Fifty Groups of VH Segments with Different Hypervariable Loops," J. Mol. Biol., vol. 227:776 (1992).
Topalian, Suzanne L. et al., "Melanoma-specific CD4+ T Cells Recognize Nonmutated HLA-DR-restricted Tyrosinase Epitopes," J. Exp. Med., vol. 183:1965-1971 (1996).
Tuaillon, N. et al, "Human Immunoglobulin Heavy-Chain Minilocus Recombination in Transgenic Mice: Gene-Segment Use in Mu and Gamma Transcripts," Proc. Natl. Acad. Sci. USA, vol. 90:3720-3724 (1993).

(56) References Cited

OTHER PUBLICATIONS

Uhlmann and Peyman, "Antisense Oligonucleotides: A new therapeutic principle," Chemical Reviews, vol. 90:544-584 (1990).

Vajdos, Felix F. et al., "Comprehensive Functional Maps of the Antigen-binding Site on an Anti-ErbB2 Antibody Obtained with Shotgun Scanning Mutagenesis," J. Mol. Biol., vol. 320:415-428 (2002).

Vlasov et al, "Arrest of immunoglobulin G mRNA translation in vitro with an alkylating antisense oligonucleotide derivative," Chemical Abstracts, p. 28, 112:229433X (1990).

Weaver et al, "A transgenic immunoglobulin Mu gene prevents rearrangement of endogenous genes," Cell, vol. 42:117-127 (1985).

Webster's New World Dictionary, Third College Edition, "Prevent," (1988).

Weiss, "Mice making human-like antibodies," The Washington Post, Apr. 28, 1994.

Wiens, Gregory D. et al., "Harmful somatic mutations: lessons from the dark side," Immunological Reviews, vol. 162:197-209 (1998).

Wood, Gary S., "Lymphocyte Activation in Cutaneous T-Cell Lymphoma," J. Invest. Dermatol., vol. 105:105S-109S (1995).

Yamamura et al, "Cell-type-specific and regulated expression of a human I1 heavy-chain immunoglobulin gene in transgenic mice," Proc. Natl. Acad. Sci. USA, vol. 83:2152-2156 (1986).

Yancopoulos and Alt, "Regulation of the assembly and expression of variable-region genes," Ann. Rev.. Immunol., vol. 4:339-368 (1986).

Yancopoulos and Alt, "Developmentally controlled and tissue-specific expression of unrearrangement VH gene segements," Cell, vol. 40:271-281 (1985).

Yasui et al, "Class switch from m to d is mediated by homologous recombination between sm and em sequences in human immunoglobulin gene loci," Eur. J. Immunol., vol. 19:1399-1403 (1989).

Zijlstra et al, "Germ-line transmission of a disrupted b2-microglobulin gene produced by homologous recombination in embryonic stem cells," Nature, vol. 342:435-438 (1989).

Zimmer and Gruss, "Production of chimaeric mice containing embryonic stem (ES) cells carrying a homoeobox Hox 1.1 allele mutated by homologous recombination," Nature, vol. 338:150-153 (1989).

Partial European Search Report for Application No. 0907555.4, dated Apr. 7, 2010.

U.S. Appl. No. 13/544,012, filed Jul. 9, 2012, Nils Lonberg.

U.S. Appl. No. 12/770,402, filed Apr. 29, 2010, Nils Lonberg, Jan. 4, 2012.

U.S. Appl. No. 13/544,012, filed Jul. 9, 2012, Nils Lonberg, Nov. 6, 2013.

U.S. Appl. No. 13/544,012, filed Jul. 9, 2012, Nils Lonberg, May 22, 2013.

Knox, Susan et al., "Treatment of Cutaneous T-Cell Lymphoma With Chimeric Anti-CD4 Monoclonal Antibody," Blood, vol. 87(3):893-899 (1996).

* cited by examiner

Figure 1

$V_H$ :
QVQLQQWGAGLLKPSETLSLTCAVYGGSFSGYYWSWIRQPPGKGLEWIGEINHSGSTNY
NPSLKSRVTISVDTSKNQFSLKLSSVTAADTAVYYCARVINWFDPWGQGTLVT $V_L$ :
DIQMTQSPSSVSASVGDRVTITCRASQDISSWLAWYQHKPGKAPKLLIYAASSLQSGVP
SRFSGSGSGTDFTLTISSLQPEDFATYYCQQANSFPYTFGQGTKLEIK

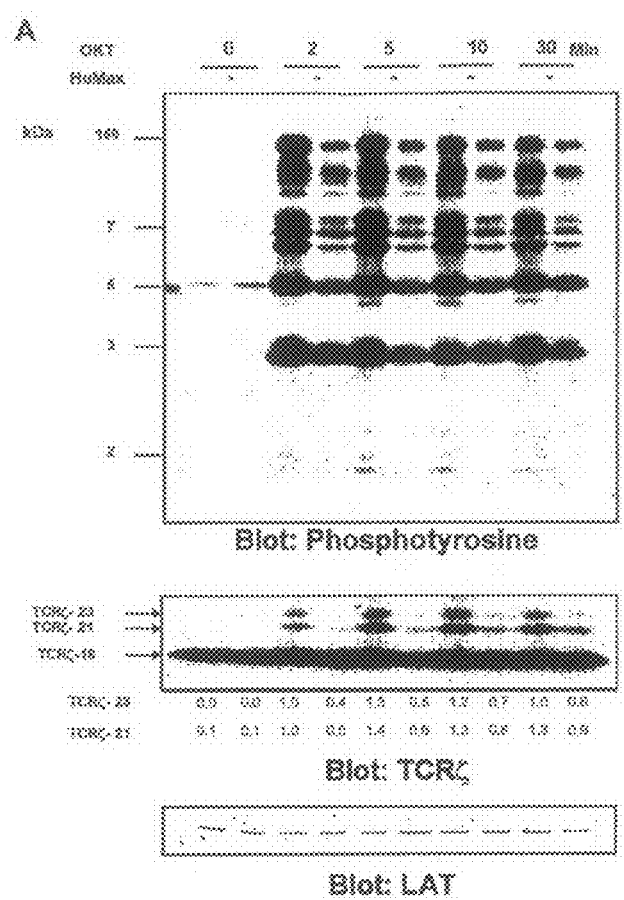

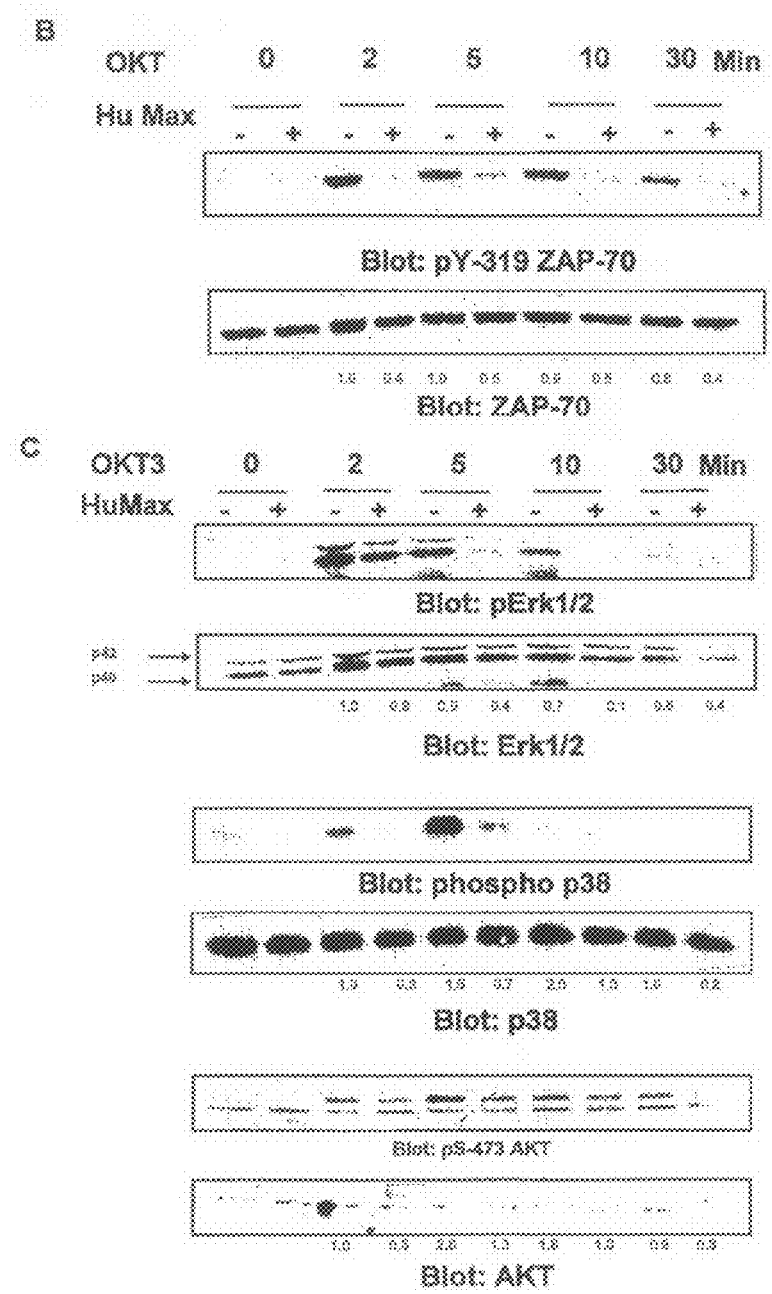

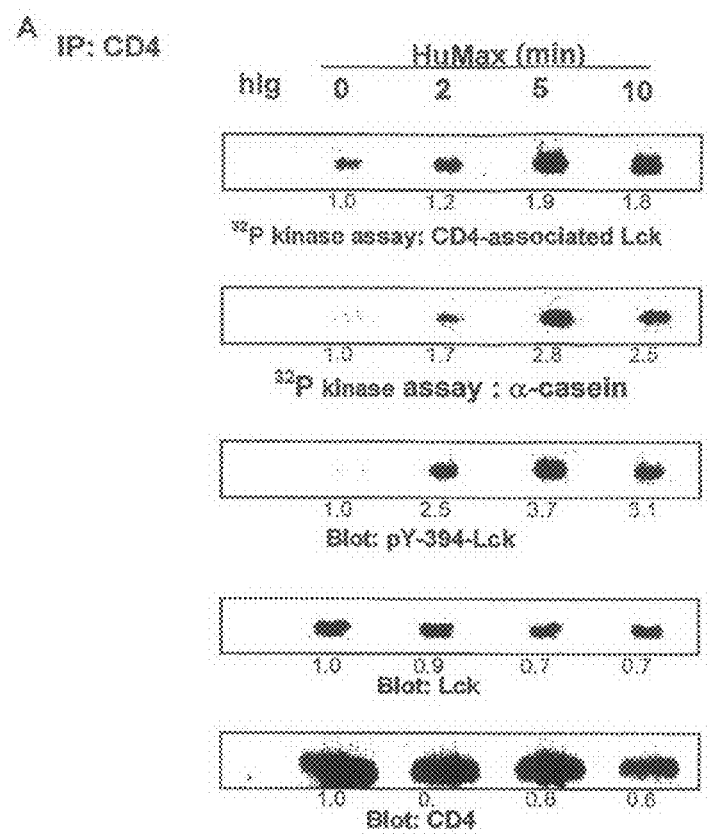

SEQUENCE LISTING

```
<160> NUMBER OF SEQ ID NOS: 2

<210> SEQ ID NO 1
<211> LENGTH: 112
<212> TYPE: PRT
<213> ORGANISM: Homo sapiens
<220> FEATURE:
<221> NAME/KEY: MISC_FEATURE
<223> OTHER INFORMATION: anti CD4 Vh

<400> SEQUENCE: 1

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Val Ile Asn Trp Phe Asp Pro Trp Gly Gln Gly Thr Leu Val Thr
            100                 105                 110

<210> SEQ ID NO 2
<211> LENGTH: 107
<212> TYPE: PRT
<213> ORGANISM: Homo sapiens
<220> FEATURE:
<221> NAME/KEY: MISC_FEATURE
<223> OTHER INFORMATION: anti CD4 VL

<400> SEQUENCE: 2

Asp Ile Gln Met Thr Gln Ser Pro Ser Ser Val Ser Ala Ser Val Gly
```

```
1               5                   10                  15
Asp Arg Val Thr Ile Thr Cys Arg Ala Ser Gln Asp Ile Ser Ser Trp
            20                  25                  30

Leu Ala Trp Tyr Gln His Lys Pro Gly Lys Ala Pro Lys Leu Leu Ile
            35              40              45

Tyr Ala Ala Ser Ser Leu Gln Ser Gly Val Pro Ser Arg Phe Ser Gly
        50              55              60

Ser Gly Ser Gly Thr Asp Phe Thr Leu Thr Ile Ser Ser Leu Gln Pro
65              70                  75                  80

Glu Asp Phe Ala Thr Tyr Tyr Cys Gln Gln Ala Asn Ser Phe Pro Tyr
                85              90              95

Thr Phe Gly Gln Gly Thr Lys Leu Glu Ile Lys
            100             105
```

THERAPY WITH CD4 BINDING PEPTIDES AND RADIATION

All patent and non-patent references cited in the application are hereby incorporated by reference in their entirety.

FIELD OF INVENTION

The present invention relates to the field of treatment of clinical conditions with radiation. In particular, the invention relates to use of peptides, such as antibodies, capable of binding CD4 for mediation of radiation treatment.

BACKGROUND OF THE INVENTION

Radiation is highly effective in inducing apoptosis in skin-infiltrating T-cells and therefore exerts beneficial effects in patients with T cell-mediated skin diseases. However, for sufficient clinical efficacy, the sensitivity of (malignant) T cells for radiation may be enhanced. After UV-exposure of lymphoma cells, an accumulation of cells in the G1 phase and an increase of the apoptotic cell fraction was observed, which was augmented by treatment with 2-AP, a G1 checkpoint inhibitor (Takemura T et al., Apoptosis. 4(4), 245-53 (1999)). This study also showed that increased expression levels of p53 in G1 phase were linked to increased sensitivity to UV-irradiation-induced cell death. Increased radiosensitivity due to elevated p53 expression in the G1 phase was supported by a number of other studies (Cuddihy A R et al., Cancer Metastasis Rev. 23(3-4), 237-57 (2004), McIlwrath A J et al., Cancer Res. 54(14), 3718-3722 (1994), Bohnke A et al., Int J Radiat Biol. 80(1), 53-63 (2004), Nagasawa M et al., Oncogene. 20(23), 2889-99 (2001)). Furthermore, squamous cell carcinoma cells were shown to be sensitized for radiation through the induction of a G1 arrest by the anti-EGFR antibody, C225 (Huang S M et al., Clin Cancer Res. 6(6), 2166-74 (2000)). Tumor cells in a G1-like quiescent phase were also found to be more sensitive to radiation than proliferating cells (Ng C E et al., Br J Cancer. 56(3), 301-307 (1987)).

Upregulation of p53 has been shown to be related to inhibition of phosphatidylinositol 3-kinase (PI3K), an important signal pathway in T cells (Grandage V L et al., Leukemia. 19(4), 586-94 (2005)). As the inhibitory adapter molecule SHIP-1 is an inhibitor of PI3K (Horn S et al., Leukemia. 18(11), 1839-49 (2004)), activation of SHIP-1 would therefore lead to upregulation of p53

Dok-1 and SHIP-1 are so called "inhibitory adaptor molecules" expressed in hematopoietic cells, which serve to attenuate signaling and thereby prevent inappropriate cellular activation (Veillette A et al., 55(2), 301-8 (1988)). Phosphorylation of Dok-1 triggers interaction with SHIP-1, which leads to negative regulation of the PI3K protein kinase B (PKB)/Akt pathway. Over-expression of Dok-1 in B cells has been shown to cause an increase in the expression of the cell cycle inhibitor $p21^{WAF1/Cip1}$, a decreased cyclin D2 expression, and a decreased expression of the anti-apoptotic protein $bcl-X_L$ (Yamakawa N et al., EMBO J. 21(7), 1684-94 (2002)). The increase of the G1/S inhibitor p21 and decrease of the G1 cyclin D would imply an extension or arrest in the G1 phase upon Dok-1 activation.

Artificially induced expression of SHIP-1, by restoration of SHIP-1 expression in endogenously SHIP-1-deficient Jurkat T cells, was shown to increase the transit time through the G1 phase. This extension of the G1 phase was associated with increased stability of cell cycle inhibitor $p27^{Kip1}$ (Horn, 2004 supra). The inhibiting influence of SHIP activation on progression through the G1 phase was confirmed by investigation of the more ubiquitously expressed homologue of SHIP-1, SHIP-2, which is also expressed in T cells (Bruyns et al., Biol. Chem. 380(7-8), 969-74 (1999)). Overexpression of SHIP-2 in glioblastoma cells inhibited the PI3K protein kinase B (PKB) pathway and caused a cell cycle arrest in G1, which was also associated with increased stability of cell cycle inhibitor $p27^{Kip1}$ (Taylor V et al., Mol Cell Biol. 20(18), 6860-6871 (2000)).

A variety of therapies that induce DNA damage, including UVB radiation, psoralen and UVA (PUVA) therapy, ionising radiation, electron beam, and x-ray (Kacinski et al., Ann N Y Acad. Sci. 941, 194-199 (2001)), and photopheresis (extracorporeal circulation of the blood with UVA and psoralen exposure) (Baron et al., Dermatol Ther. 16(4), 303-310 (2003)) have been indicated for CTCL.

PUVA is a highly effective treatment for cutaneous disease caused by skin infiltration with normal or neoplastic T-lymphocytes. It was reported that T-lymphocytes were greater than 50 fold more sensitive to cytotoxic effect of PUVA than other skin-resident cells such as keratinocytes (Johnson et al., Photochem Photobiol. 63(5), 566-571 (1996). A sub-G1 DNA peak indicated that cell death occurred by apoptosis and PUVA treatment markedly slowed cell cycle progression, eventually producing cell cycle arrest and apoptotic entry (Johnson R et al., Photochem Photobiol. 63(5), 566-571 (1996)). It has also been shown that PUVA leads to cross-links between DNA strands in the irradiated skin and that the damaged DNA will activate DNA repair mechanisms and cells are arrested in the G2 phase of the cell cycle in epidermal cells (Hashimoto Y et al., J Dermatol Sci. 10(1), 16-24 (1995) or fibroblasts (Ma W et al., Exp Dermatol. 12(5), 629-37 (2003).

SUMMARY OF INVENTION

The present invention relates to the surprising finding that antibodies capable of binding to CD4 may induce increased phosphorylation of $p56^{Ick}$. In addition, phosphorylation of p56Ick by anti-CD4 monoclonal antibody zanolimumab has been linked to increased phosphorylation of certain substrates of $p56^{Ick}$ tyrosine kinase, for example of the inhibitory adapter molecules Dok-1 and/or SHIP-1. Activation of these inhibitory adapter molecules often results in a cell cycle extension or arrest in the G1 phase. Cells arrested in the G1 phase may be sensitized for radiation treatment (McIlwrath 1994 supra) thus enhancing efficacy of a subsequent or concurrent radiation treatment. Also, the activation of the inhibitory adaptor molecules, like SHIP-1 often results in the inhibition of PI3k, which often results in upregulation of p53, and thereby may facilitate apoptosis in T cells upon radiotherapy (Okkenhaug K. et al., Nature reviews 3, 317-330 (2003)).

In one embodiment, the present invention relates to a peptide, such as an antibody, capable of binding to CD4 and use thereof for the mediation of radiation treatment of a clinical condition. In the context of the present invention, peptides capable of binding to CD4 may also be termed "CD4 binding peptides" and antibodies capable of binding to CD4 may also be termed "anti-CD4 antibodies". In one embodiment, CD4 binding peptides, such as anti-CD4 antibodies or antigen binding fragments thereof, for use according to the present invention are capable of one or more of the following, for instance at least 2 of the following, such as at least 3 of the following, for instance at least 4 of the following, such as at least 5 of the following, for instance at least 6 of the following, such as at least 7 of the following, for instance at least 8 of the following, such as all of the following:

inducing phosphorylation of α-casein by p56$^{lck}$
inducing p56$^{lck}$ autophosphorylation,
inducing phosphorylation of inhibitory adapter molecules Dok-1 and/or SHIP-1 and/or SHIP-2,
inducing p56$^{lck}$-mediated Dok-1 phosphorylation,
inhibition of the PKB/Akt pathway,
sequestration of CD4 away from the TCR,
increasing and/or up-regulating p53 expression,
inducing arrest or extension of the G1 phase of the cell cycle.
increasing CD4$^+$ cell, preferably CD4$^+$ T cell sensitivity to radiation.

CD4 binding peptides, such as anti-CD4 antibodies or antigen binding fragments thereof, for use according to the present invention are capable of binding to CD4 and thereby inducing phosphorylation of certain substrates of p56$^{lck}$ tyrosine kinase. Activation of p56$^{lck}$ tyrosine kinase in general leads to increased expression of inhibitory adapter proteins downstream of tyrosine kinase (Dok-1) (Martelli M P et al., J Biol. Chem. 276(49), 45654-45661 (2001), Okabe S et al., Blood. 105(2), 474-480 (2005)) and/or SH2 domain contacting 5'-inositol phasphatase (SHIP-1) by phosphorylation (Lamkin T D et al., J Biol. Chem. 272(16), 10396-401 (1997)). Dok-1 and SHIP-1 are expressed, for example, in haematopoietic cells, where they may serve to attenuate signaling and thereby prevent inappropriate cellular activation (Veillette et al., Annu Rev Immunol. 20, 669-707 (2002)). The phosphorylation of Dok-1 and SHIP-1, in general, lead to inhibition of ras/ERK and AKT pathways. The activation of Dok-1 may trigger interaction with SHIP-1, which may lead to negative regulation of PI3K protein kinase B (PKB)/Akt pathway thus arresting cell cycle in G1 phase. Over-expression of Dok-1 in B cells decreases cyclin D2 expression and/or increases cell cycle inhibitor p21$^{WAF1/Chip1}$ expression (Yamakawa 2002 supra), both leading to extension or arrest in G1 phase. Activation and expression of SHIP-1 induces increased transit time through G1 phase and increase in stability of the cell cycle inhibitor p27$^{Kip1}$ (Horn, 2004 supra). SHIP-1 homologue SHIP-2 is ubiquitously expressed and the over-expression of SHIP-2 leads to the inhibition of PI3K protein kinase B (PKB) pathway thus arresting the cell cycle in G1 phase (Taylor V 2000 supra). The expression of SHIP-1 inhibits, in addition, PI3K protein kinase B (Horn, 2004 supra) which can lead to up-regulation of p53 (Grandage 2005 supra). Tumor cells expressing p53 are arrested in G1 phase (Bohnke 2004 supra) and, in addition, functional p53 facilitates apoptosis in lymphocytes upon radiation (Cuddihy 2004 supra).

Cells in G1 phase are often more sensitive to ionizing radiation (McIlwrath 1994 supra) and furthermore, tumor cells in G1-like quiescent phase are more sensitive to radiation than proliferating cells (Ng 1987 supra). The binding of CD4 binding peptides, such as anti-CD4 antibodies or antigen binding fragments thereof, to a CD4$^+$ T cell therefore may sensitize cells to radiation treatment and induce apoptosis of cells following such treatment.

In one embodiment, the invention relates to a CD4 binding peptide, such as an anti-CD4 antibody or antigen binding fragment thereof, for the treatment of a malignant disease or an inflammatory skin disease in an individual who receives or will receive radiation treatment.

In one embodiment, the invention relates to a CD4 binding peptide, such as an anti-CD4 antibody or antigen binding fragment thereof, for the treatment of a malignant disease or an inflammatory skin disease in combination with radiation treatment.

In one embodiment, the invention relates to a CD4 binding peptide, such as an anti-CD4 antibody or antigen binding fragment thereof, for the mediation of radiation treatment of a clinical condition.

In one embodiment, the invention relates to the use of a CD4 binding peptide, such as an anti-CD4 antibody or antigen binding fragment thereof, in the preparation of a pharmaceutical composition for the treatment of a malignant disease or an inflammatory skin disease in an individual who receives or will receive radiation treatment.

In one embodiment, the invention relates to use of a CD4 binding peptide, such as an anti-CD4 antibody or antigen binding fragment thereof, in the preparation of a pharmaceutical composition for the treatment of a malignant disease or an inflammatory skin disease in combination with radiation treatment.

In one embodiment, the invention relates to use of a CD4 binding peptide, such as an anti-CD4 antibody or antigen binding fragment thereof, capable of binding to CD4 in the preparation of a pharmaceutical composition for the mediation of radiation treatment of a clinical condition.

In one embodiment, the invention relates to a method of treatment of malignant disease or an inflammatory skin disease comprising administering to a subject in need thereof a therapeutically effective amount of a CD4 binding peptide, such as an anti-CD4 antibody or antigen binding fragment thereof, and subjecting said subject to radiation treatment.

In one embodiment, the invention relates to a method of mediating radiation treatment of a clinical condition comprising administering to a subject in need thereof a therapeutically effective amount of a CD4 binding peptide, such as an anti-CD4 antibody or antigen binding fragment thereof, and subjecting said subject to radiation treatment.

In one embodiment, the invention relates to a kit of parts comprising a CD4 binding peptide, such as an anti-CD4 antibody or antigen binding fragment thereof, and a psoralen together with one or more pharmaceutically acceptable excipients for use as a medicament.

In one embodiment, the invention relates to a kit of parts comprising a CD4 binding peptide, such as an anti-CD4 antibody or antigen binding fragment thereof, and a psoralen together with pharmaceutically acceptable excipients for use as a medicament in the treatment of a malignant disease or an inflammatory skin disease.

In one embodiment, the invention relates to a kit of parts comprising a CD4 binding peptide, such as an anti-CD4 antibody or antigen binding fragment thereof, and a psoralen together with pharmaceutically acceptable excipients for use as a medicament in the treatment of a malignant disease or an inflammatory skin disease in combination with radiation treatment.

In one embodiment, the present invention relates to the use of a CD4 binding peptide, such as an anti-CD4 antibody or antigen binding fragment thereof, and a psoralen in the preparation of a pharmaceutical kit of parts for the treatment of a malignant disease or an inflammatory skin disease. The kit of parts may comprise the CD4 binding peptide in multiple dosage form or in unit dosage form. Similar, the kit of parts may comprise the psoralen in multiple dosage form or in unit dosage form. Suitable unit dosages are described herein below.

In one embodiment, the present invention relates to the use of a CD4 binding peptide, such as an anti-CD4 antibody or antigen binding fragment thereof, and a psoralen in the preparation of a pharmaceutical kit of parts for use in combination with radiation in the treatment of a malignant disease or an inflammatory skin disease. The kit of parts may comprise the CD4 binding peptide in multiple dosage form or in unit dosage form. Similar, the kit of parts may comprise the psoralen in multiple dosage form or in unit dosage form. Suitable unit dosages are described herein below.

DESCRIPTION OF FIGURES

FIG. 1 shows the VH (SEQ ID NO: 1) and VL (SEQ ID NO: 2) sequences of 6G5 from WO97/13852.

FIG. 2 illustrates results of Western blotting of cell lysates prepared from CD4$^+$ T cells stimulated with CD3 monoclonal antibody and zanolimumab. CD4$^+$ T cells were incubated with HuMax-CD4 and then stimulated with CD3 monoclonal antibody (OKT3) immobilized onto latex beads. Proteins in duplicate cell lysate samples were separated by 7-15% gradient gel SDS-PAGE and were transferred onto blotting membranes by electrophoresis. One membrane was incubated with a phosphotyrosine specific antibody, stripped and then re-probed with TCRζ and LAT specific antibodies (FIG. 2A). The other was incubated with antibodies to the phosphorylated form of specific proteins, stripped and then re-probed with ZAP-70 (2B), Erk1/2, p38 and AKT antibodies (2C). The numbers below the blots represent densitometric values normalized for loading relative to values observed after 2 min of CD3-stimulation in the absence of HuMax-CD4. Results for the experiments shown here are representative of 4 independent experiments.

FIG. 3A: Two CD4-precipitates were submitted to a kinase assay (upper two panels). Blots were probed with antibodies to $p56^{lck}$ (top panel), the $p56^{lck}$ substrate α-casein (second panel), Y-394 phosphorylated $p56^{lck}$ (third panel), $p56^{lck}$ (fourth panel) or CD4 (bottom panel). The numbers below the blots represent densitometric values normalized for $p56^{lck}$ loading. FIG. 3B: Blots with SH2-precipitate were incubated with antibodies to Dok-1 (top panel) or GST (bottom panel). The numbers below the blots represent densitometric values normalized for GST loading. FIG. 3C: Proteins in whole cell lysate were separated by SDS-PAGE and blotted. Membranes were incubated with antibodies to phosphorylated SHIP-1 (top panel) or SHIP-1 regardless of phosphorylation status (bottom panel). The numbers below the blots represent densitometric values normalized for SHIP-1 loading. FIG. 3D: Before zanolimumab exposure, cells were pre-incubated with Src kinase inhibitors PP2 or damnacanthal (DAM). Blots were incubated with antibodies for Dok-1 (top panel) or GST (bottom panel). The numbers below the blots represent densitometric values normalized for GST loading. Results for the experiments shown here are representative of 4 independent experiments.

DETAILED DESCRIPTION OF THE INVENTION

Figure 3:
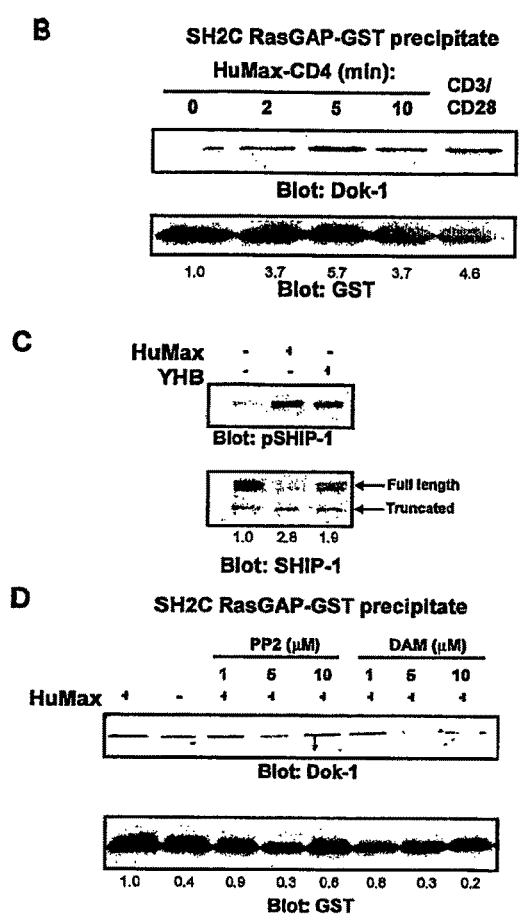
FIG. 3 illustrates results from CD4$^+$ T cells incubated with zanolimumab or a human immunoglobulin negative control. Cell lysates were CD4-precipitated (A), SH2-precipitated (B, D) or used as whole lysate (C).

The present invention provides methods and uses of a CD4 binding peptide, such as an anti-CD4 antibody or antigen binding fragment thereof, or a kit of parts comprising said CD4 binding peptide for improved treatment of malignant disease or an inflammatory skin disease comprising using the CD4 binding peptide in combination with radiation and/or a psoralen.

In one embodiment, the invention relates to a CD4 binding peptide, such as an anti-CD4 antibody or antigen binding fragment thereof, for the treatment of a malignant disease or an inflammatory skin disease in an individual who receives or will receive radiation treatment.

In one embodiment, the invention relates to a CD4 binding peptide, such as an anti-CD4 antibody or antigen binding fragment thereof, for the treatment of a malignant disease or an inflammatory skin disease in combination with radiation treatment.

In one embodiment, the invention relates to the use of a CD4 binding peptide, such as an anti-CD4 antibody or antigen binding fragment thereof, in the preparation of a pharmaceutical composition for the treatment of a malignant disease or an inflammatory skin disease in an individual who receives or will receive radiation treatment.

In one embodiment, the invention relates to use of a CD4 binding peptide, such as an anti-CD4 antibody or antigen binding fragment thereof, in the preparation of a pharmaceutical composition for the treatment of a malignant disease or an inflammatory skin disease in combination with radiation treatment.

In one embodiment, the invention relates to a method of treatment of malignant disease or an inflammatory skin disease comprising administering to a subject in need thereof a therapeutically effective amount of a CD4 binding peptide, such as an anti-CD4 antibody or antigen binding fragment thereof, and subjecting said subject to radiation treatment.

In one embodiment, the invention relates to a kit of parts comprising a CD4 binding peptide, such as an anti-CD4 antibody or antigen binding fragment thereof, and a psoralen together with pharmaceutically acceptable excipients for use as a medicament.

In one embodiment, the invention relates to a kit of parts comprising a CD4 binding peptide, such as an anti-CD4 antibody or antigen binding fragment thereof, and a psoralen together with pharmaceutically acceptable excipients for use as a medicament in the treatment of a malignant disease or an inflammatory skin disease.

In one embodiment, the invention relates to a kit of parts comprising a CD4 binding peptide, such as an anti-CD4 antibody or antigen binding fragment thereof, and a psoralen together with pharmaceutically acceptable excipients for use as a medicament in the treatment of a malignant disease or an inflammatory skin disease in combination with radiation treatment.

In one embodiment, the present invention relates to the use of a CD4 binding peptide, such as an anti-CD4 antibody or antigen binding fragment thereof, and a psoralen in the preparation of a pharmaceutical kit of parts for the treatment of a malignant disease or an inflammatory skin disease. The kit of parts may comprise the CD4 binding peptide in multiple dosage form or in unit dosage form. Similar, the kit of parts may comprise the psoralen in multiple dosage form or in unit dosage form. Suitable unit dosages are described herein below.

In one embodiment, the present invention relates to the use of a CD4 binding peptide, such as an anti-CD4 antibody or antigen binding fragment thereof, and a psoralen in the preparation of a pharmaceutical kit of parts for use in combination with radiation in the treatment of a malignant disease or an inflammatory skin disease. The kit of parts may comprise the CD4 binding peptide in multiple dosage form or in unit dosage form. Similar, the kit of parts may comprise the psoralen in multiple dosage form or in unit dosage form. Suitable unit dosages are described herein below.

In one embodiment, the compounds of the present invention are used for treatment of treatment refractory disease. In one embodiment, a compound of the present invention is used for treatment of a cancer or an inflammatory skin disease wherein the disease is resistant to another treatment modality.

The term peptide with respect to CD4 binding peptides as described herein includes any suitable peptide capable of binding CD4 and may be used synonymously with the terms polypeptide and protein, unless otherwise stated or contradicted by context; provided that the reader recognize that each type of respective amino acid polymer-containing molecule can be associated with significant differences and thereby form individual embodiments of the present invention (for example, a peptide such as an antibody, which is composed of multiple polypeptide chains, is significantly different from, for example, a single chain antibody, a peptide immunoadhesin, or single chain immunogenic peptide). Therefore, the term peptide herein should generally be understood as referring to any suitable peptide of any suitable size and composition (with respect to the number of amino acids and number of associated chains in a protein molecule). Moreover, peptides in the context of the inventive methods and compositions described herein may comprise non-naturally occurring and/or non-L amino acid residues, unless otherwise stated or contradicted by context.

As will be discussed further herein, unless otherwise stated or contradicted by context, the term peptide (and if discussed as individual embodiments of the term(s) polypeptide and/or protein) also encompasses derivatized peptide molecules. Briefly, in the context of the present invention, a derivative is a peptide in which one or more of the amino acid residues of the peptide have been chemically modified (for instance by alkylation, acylation, ester formation, or amide formation) or associated with one or more non-amino acid organic and/or inorganic atomic or molecular substituents (for instance a polyethylene glycol (PEG) group, a lipophilic substituent (which optionally may be linked to the amino acid sequence of the peptide by a spacer residue or group such as β-alanine, γ-aminobutyric acid (GABA), L/D-glutamic acid, succinic acid, and the like), a fluorophore, biotin, a radionuclide, etc.) and may also or alternatively comprise non-essential, non-naturally occurring, and/or non-L amino acid residues, unless otherwise stated or contradicted by context (however, it should again be recognized that such derivatives may, in and of themselves, be considered independent features of the present invention and inclusion of such molecules within the meaning of peptide is done for the sake of convenience in describing the present invention rather than to imply any sort of equivalence between naked peptides and such derivatives). Non-limiting examples of such amino acid residues include for instance 2-aminoadipic acid, 3-aminoadipic acid, β-alanine, β-aminopropionic acid, 2-aminobutyric acid, 4-aminobutyric acid, 6-aminocaproic acid, 2-aminoheptanoic acid, 2-aminoisobutyric acid, 3-aminoisobutyric acid, 2-aminopimelic acid, 2,4-diaminobutyric acid, desmosine, 2,2'-diaminopimelic acid, 2,3-diaminopropionic acid, N-ethylglycine, N-ethylasparagine, hydroxylysine, allohydroxylysine, 3-hydroxyproline, 4-hydroxy-proline, isodesmosine, alloisoleucine, N-methylglycine, N-methylisoleucine, 6-N-methyllysine, N-methylvaline, norvaline, norleucine, ornithine, and statine halogenated amino acids.

CD4 binding peptides refers to any peptide that specifically binds to a portion of CD4 under cellular and/or physiological conditions for an amount of time sufficient to induce, promote, enhance, and/or otherwise modulate a physiological effect associated with CD4; to allow detection by ELISA, Western blot, or other similarly suitable protein binding technique described herein and/or known in the art and/or to otherwise be detectably bound thereto after a relevant period of time (for instance at least about 15 minutes, at least about 30 minutes, at least about 45 minutes, at least about 1 hour, at least about 2 hours, at least about 4 hours, at least about 6 hours, at least about 12 hours, about 1-24 hours, about 1-36 hours, about 1-48 hours, about 1-72 hours, about one week, or longer).

A CD4 binding peptide is a peptide that binds specifically to CD4. A CD4 binding peptide for use according to the present invention may be prepared by any method for peptide preparation known in art, such as synthetic production or recombinant production.

A CD4 binding antibody, or anti-CD4 antibody or functional equivalent thereof may be any form of antibody known in the art, for example native antibodies derived from a mammal or a synthetic antibody, such as a single chain antibody, diabodies, monovalent antibodies or hybrids comprising antibody fragments, which are capable of binding specifically to CD4, such as human CD4. Furthermore, the antibody may be mixtures of monoclonal antibodies or artificial polyclonal antibodies.

An antibody that is contemplated for use in the present invention thus can be in any of a variety of forms, including a native antibody, whole immunoglobulin, an antibody fragment such as Fv, Fab, Fab', F(ab')$_2$ and similar fragments, a single chain antibody which includes the variable domain complementarity determining regions (CDR), diabodies and all of which fall under the broad term "antibody", as used herein. An antibody may also be murine, chimeric, humanized or human under the broad term "antibody", as used herein.

The term "native antibody" as used herein as applied to antibodies of a structure similar to the structure of antibodies found in nature. Native antibodies for use according to the present invention belong to a family of plasma proteins called immunoglobulins, whose basic building block, the immunoglobulin fold or domain, is used in various forms in many molecules of the immune system and other biological recognition systems. A typical immunoglobulin has four polypeptide chains, containing an antigen binding region known as a variable region and, for each antibody (sub) class, a non-varying region known as the constant region.

As used herein, native antibodies and immunoglobulins are usually heterotetrameric glycoproteins of about 150,000 daltons, composed of two identical light (L) chains and two identical heavy (H) chains. Typically, each light chain is linked to a heavy chain by one or more covalent disulfide bond, while the number of disulfide linkages varies between the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end. The constant domain of the light chain is paired with the first constant domain of the heavy chain, and the light chain variable domain is paired with the variable domain of the heavy chain. Particular amino acid residues are believed to form an interface between the light and heavy chain variable domains (Novotny J, & Haber E. Proc Natl Acad Sci USA. 82(14):4592-6, 1985).

Depending on the amino acid sequences of the constant domain of their heavy chains, immunoglobulins can be assigned to different classes. There are at least five (5) major classes of immunoglobulins: IgA, IgD, IgE, IgG and IgM, and several of these may be further divided into subclasses (isotypes), for instance IgG1, IgG2, IgG3 and IgG4; IgA1 and IgA2. The heavy chains constant gene segments that encode the different classes of immunoglobulins are called alpha (α), delta (δ), epsilon (ε), gamma (γ) and mu (μu), respectively.

The light chains of antibodies can be assigned to one of two clearly distinct types, called kappa (κ) and lambda (λ), based on the amino sequences of their constant domain. The subunit structures and three-dimensional configurations of different classes of immunoglobulins are well known.

The term "variable" in the context of variable domain of antibodies, refers to the fact that certain portions of the variable domains differ extensively in sequence among antibodies. The variable domains are for binding and determine the specificity of each particular antibody for its particular antigen. However, the variability is not evenly distributed through the variable domains of antibodies. It is concentrated in three segments called complementarity determining regions (CDRs) also known as hypervariable regions both in the light chain and in the heavy chain variable domains.

The more highly conserved portions of variable domains are called the framework (FR). The variable domains of native heavy and light chains each comprise four FR regions, largely adopting a β-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the antigen-binding site of antibodies. The constant domains are not involved directly in binding an antibody to an antigen, but exhibit various effector functions, such as participation of the antibody in antibody-dependent cellular toxicity.

The term "antibody fragment" refers to a portion of a full-length antibody, generally the antigen binding or variable region. Examples of antibody fragments include Fab, Fab', F(ab')$_2$ and Fv fragments. Papain digestion of antibodies produces two identical antigen binding fragments, called the Fab fragment, each with a single antigen binding site, and a residual "Fc" fragment, so-called for its ability to crystallize readily. Pepsin treatment yields an F(ab')$_2$ fragment that has two antigen binding fragments that are capable of cross-linking antigen, and a residual other fragment (which is termed pFc'). Additional fragments can include diabodies, linear antibodies, single-chain antibody molecules, and multispecific antibodies formed from antibody fragments.

The term "antibody fragment" is used herein interchangeably with the term "antigen binding fragment".

Antibody fragments retain some ability to bind to its antigen. Some types of antibody fragments are defined as follows:
(1) Fab is the fragment that contains a monovalent antigen-binding fragment of an antibody molecule. A Fab fragment can be produced by digestion of whole antibody with the enzyme papain to yield an intact light chain and a portion of one heavy chain.
(2) Fab' is the fragment of an antibody molecule can be obtained by treating whole antibody with pepsin, followed by reduction, to yield an intact light chain and a portion of the heavy chain. Two Fab' fragments are obtained per antibody molecule. Fab' fragments differ from Fab fragments by the addition of a few residues at the carboxyl terminus of the heavy chain CH1 domain including one or more cysteines from the antibody hinge region.
(3) (Fab')$_2$ is the fragment of an antibody that can be obtained by treating whole antibody with the enzyme pepsin without subsequent reduction.
(4) F(ab')$_2$ is a dimer of two Fab' fragments held together by two disulfide bonds.

Fv is the small antibody fragment that contains a complete antigen recognition and binding site. This region consists of a dimer of one heavy and one light chain variable domain in a tight, non-covalent association ($V_H$-$V_L$ dimer). It is in this configuration that the three CDRs of each variable domain interact to define an antigen binding site on the surface of the $V_H$-$V_L$ dimer. Collectively, the six CDRs confer antigen binding specificity to the antibody. However, even a single variable domain (or half of an Fv comprising only three CDRs specific for an antigen) may have the ability to recognize and bind antigen, although frequently lower affinity than the entire binding site. Even a single CDR, notably CDR3 domain, most notably the CDR3 domain of the heavy chain may be sufficient for antigen recognition (see for example Deng and Notkins, 2000, Clin. Exp. Immunol. 119:69-76). Thus it is comprised within the present invention that the antigen binding fragment of an antibody may comprise a single variable domain or even a single CDR, for instance CDR3, such as CDR3 of the heavy chain in one or more copies.

Single chain antibody ("SCA"), defined as a genetically engineered molecule containing the variable region of the light chain, the variable region of the heavy chain, linked by a suitable polypeptide linker as a genetically fused single chain molecule. Such single chain antibodies are also referred to as "single-chain Fv" or "sFv" antibody fragments. Generally, the Fv polypeptide further comprises a polypeptide linker between the VH and VL domains that enables the sFv to form the desired structure for antigen binding. For a review of sFv, see Pluckthun in "The Pharmacology of Monoclonal Antibodies" 113, 269-315 Rosenburg and Moore eds. Springer-Verlag, NY, 1994.

Antibodies for use according to the present invention may also be diabodies. "Diabodies" refers to a small antibody fragments with two antigen-binding sites, which fragments comprise a heavy chain variable domain (VH) connected to a light chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies are described more fully in, for example, EP 404097; WO 93/11161, and Hollinger et al., Proc. Natl. Acad. Sci. USA 90, 6444-6448 (1993).

The invention contemplate both polyclonal and monoclonal antibody against CD4 and antigen binding fragments and thereof which possess at least one or more of the following, for instance at least 2 of the following, such as at least 3 of the following, for instance at least 4 of the following, such as at least 5 of the following, for instance at least 6 of the following, such as at least 7 of the following, for instance at least 8 of the following, such as all of the following:
 inducing phosphorylation of α-casein by $p56^{lck}$,
 inducing $p56^{lck}$ autophosphorylation,
 inducing phosphorylation of inhibitory adapter molecules Dok-1 and/or SHIP-1 and/or SHIP-2,
 inducing $p56^{lck}$-mediated Dok-1 phosphorylation,
 inhibition of the PKB/Akt pathway,
 sequestration of CD4 away from the TCR,
 increasing and/or up-regulating p53 expression,
 inducing arrest or extension of the G1 phase of the cell cycle.
 increasing CD4$^+$ cell, preferably CD4$^+$ T cell sensitivity to radiation.

The preparation of polyclonal antibodies is well-known to those skilled in the art. See, for example, Green et al. "Production of Polyclonal Antisera", in: Immunochemical Protocols (Manson, ed.), pages 1-5 (Humana Press, 1992); Coligan, et al., "Production of Polyclonal Antisera in Rabbits, Rats Mice and Hamsters" in Current Protocols in Immunology, section 2.4.1, which are hereby incorporated by reference.

The preparation of monoclonal antibodies likewise is conventional. See, for example, Kohler & Milstein, Nature 256, 495-497 (1975); Coligan et al., supra sections 2.5.1-2.6.7; and Harlow, et al., in "Antibodies: A Laboratory Manual", page 726, Cold Spring Harbor Pub. (1988). Monoclonal antibodies can be isolated and purified from hybridoma cultures by a variety of well-established techniques. Such isolation techniques include affinity chromatography with Protein-A Sepharose, size-exclusion chromatography, and ion-exchange chromatography. See, for instance Coligan et al., supra sections 2.7.1-2.7.12 and sections 2.9.1-2.9.3; Barnes, et al., "Purification of Immunoglobulin G (IgG)" in: Methods in Molecular Biology, 10, 79-104, Humana Press, NY (1992).

Methods of in vitro and in vivo manipulation of monoclonal antibodies are well known to those skilled in the art. For example, the monoclonal antibodies to be used in accordance with the present invention may be made by the hybridoma method first described by Kohler & Milstein, Nature 256, 495-497 (1975), or may be made by recombinant methods. The monoclonal antibodies for use with the present invention may also be isolated from phage antibody libraries using the techniques described in Clackson et al., Nature 352, 624-628 (1991), as well as in Marks et al., J Mol Biol 222, 581-597 (1991). Another method involves humanizing a monoclonal antibody by recombinant means to generate antibodies containing human specific and recognizable sequences. See, for review, Holmes et al., J Immunol 158, 2192-2201 (1997) and Vaswani, et al., Annals Allergy, Asthma & Immunol 81, 105-115 (1998).

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site or epitope. Furthermore, in contrast to conventional polyclonal antibody preparations that typically include different antibodies directed against different determinants (epitopes), each monoclonal antibody is directed against a single determinant on the antigen. In additional to their specificity, the monoclonal antibodies are advantageous in that they are synthesized by the hybridoma culture, uncontaminated by other immunoglobulins. The modifier "monoclonal" indicates the character of the antibody indicates the character of the antibody as being obtained from a substantially homogeneous population of antibodies, and is not to be construed as requiring production of the antibody by any particular method.

The monoclonal antibodies herein include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567); Morrison et al., Proc Natl Acad Sci 81, 6851-6855 (1984).

In one embodiment, the antibodies herein include antibodies capable of activating antibody-dependent cell-mediated cytotoxicity (ADCC). In a further embodiment the antibodies herein include antibodies capable of activating natural killer (NK) cells. In one embodiment, the antibodies herein include antibodies capable of interacting with FcγRIII (CD16) receptor on NK cells. In one further embodiment, the antibodies herein are of subtype IgG1 or IgG3.

Methods of making antibody fragments are also known in the art (see for example, Harlow, et al., in "Antibodies: A Laboratory Manual", page 726, Cold Spring Harbor Pub. (1988), incorporated herein by reference). Antibody fragments of the present invention can be prepared by proteolytic hydrolysis of the antibody or by expression in $E.\ coli$ of DNA encoding the fragment. Antibody fragments can be obtained by pepsin or papain digestion of whole antibodies conventional methods. For example, antibody fragments can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, in U.S. Pat. Nos. 4,036,945 and 4,331,647, and references contained therein. These patents are hereby incorporated in their entireties by reference. Antibody fragments may also be prepared using recombinant techniques.

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody. For example, Fv fragments comprise an association of $V_H$ and $V_L$ chains. This association may be non-covalent or the variable chains can be linked by an intermolecular disulfide bond or cross-linked by chemicals such as glutaraldehyde. The Fv fragments may for instance comprise $V_H$ and $V_L$ chains connected by a peptide linker. These single-chain antigen binding proteins (sFv) are prepared by constructing a structural gene comprising DNA sequences encoding the $V_H$ and $V_L$ domains connected by an oligonucleotide. The structural gene is inserted into an expression vector, which is subsequently introduced into a host cell such as $E.\ coli$. The recombinant host cells synthesize a single polypeptide chain with a linker peptide bridging the two V domains. Methods for producing sFvs are described, for example, by Whitlow, et al., in: "Methods: A Companion to Methods in Enzymology", 2, 97 (1991); Bird et al., Science 242, 423-426 (1988), U.S. Pat. No. 4,946,778; and Pack et al., BioTechnology 11, 1271-1277 (1993).

Another form of an antibody fragment is a peptide coding for a single complementarity-determining region (CDR), for instance a CDR3. CDR peptides ("minimal recognition units") are often involved in antigen recognition and binding. CDR peptides can be obtained by cloning or constructing genes encoding the CDR of an antibody of interest. Such genes are prepared, for example, by using the polymerase chain reaction to synthesize the variable region from RNA of antibody-producing cells. See, for example, Larrick, et al., "Methods: a Companion to Methods in Enzymology", Vol. 2, page 106 (1991).

The invention also contemplates use of human or humanized forms of non-human (for instance murine or rat) antibodies. Such humanized antibodies are chimeric immunoglobulins, immunoglobulin chains or fragments thereof (such as Fv, Fab, Fab', F(ab')$_2$ or other antigen-binding subsequences of antibodies) that contain a minimal sequence derived from non-human immunoglobulin, such as the epitope recognizing sequence. For the most part, humanized antibodies are human immunoglobulins (recipient antibody) in which residues from one or more complementary determining region (CDR) of the recipient are replaced by residues from one or more CDR(s) of a nonhuman species (donor antibody) such as mouse, rat or rabbit having the desired specificity, affinity and capacity.

In one embodiment, the monoclonal antibodies are "human" antibodies (immunoglobulins). Human antibodies may for example be prepared using transgenic non-human animals. Such animals are used to produce heterologous antibodies and useful methods are well known to those skilled in the art. The construction of transgenic animals harboring a functional heterologous immunoglobulin transgene is one method by which antibodies reactive with self antigens may be produced. First, the immunized animal that serves as the source of B cells must make an immune response against the presented antigen. In order for an animal to make an immune response, the antigen presented must be foreign and the animal must not be tolerant to the antigen. According to the present invention, the antigen is CD4, for instance human CD4 or a fragment thereof or a (poly)peptide comprising at least one epitope of CD4. Examples of suitable methods for preparation of human antibodies are described, for example, in WO 97/13852, page 80 to 98 under "Specific preferred embodiment" and in references contained therein. In one embodiment, the present invention relates to monoclonal, human antibodies capable of binding to CD4.

In some instances, Fv framework residues of the human immunoglobulin are replaced by corresponding non-human residues. Furthermore, humanized antibodies may comprise residues that are found neither in the recipient antibody nor in an imported CDR or framework sequences. These modifications are made to further refine and optimize antibody performance. Frequently, humanized antibodies will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin. For further details, see: Jones et al., Nature 321, 522-525 (1986); Reichmann et al., Nature 332, 323-329 (1988); Presta, Curr Op Struct Biol 2, 593-596 (1992); Holmes et al., J Immunol 158, 2192-2201 (1997) and Vaswani 1998 supra).

The generation of antibodies may be achieved by any standard methods in the art for producing polyclonal and monoclonal antibodies using a natural or recombinant human CD4 polypeptide or fragments thereof as an antigen. In one embodiment, such antibodies may be generated using a naturally occurring or recombinantly produced CD4, a fragment of CD4 or a (poly)peptide comprising at least one epitope found on native CD4. Said CD4 may for instance be human CD4.

In one embodiment, the invention relates to a CD4 binding peptide, such as an anti-CD4 antibody or antigen binding fragment thereof, which is capable of inhibiting biological function of CD4 in connection with cell cycle regulation.

In one embodiment, the invention relates to a CD4 binding peptide, such as an anti-CD4 antibody or antigen binding fragment thereof, which is capable of binding to a specific epitope on CD4 as described herein and thereby inhibiting the function of CD4 protein in association with cell cycle regulation.

By the term "epitope" is meant the specific group of amino acids (on an antigen molecule) that is recognized by antibodies directed at that antigen. The term "epitope" is the equivalent to the term "antigenic determinant". The epitope may comprise 3 or more amino acid residues, such as for example 4, 5, 6, 7, 8 amino acid residues, located in close proximity, such as within a contiguous amino acid sequence, or located in distant parts of the amino acid sequence of an antigen, but due to protein folding have been approached to each other.

An antibody for use according to the present invention is capable of binding an epitope of CD4, such as of human CD4 (for sequence of human CD4, see for instance (Maddon P J et al., Cell. 42(1), 93-104 (1985)). In one embodiment, the epitope is positioned in the extracellular domain of CD4. In one embodiment, the epitope is positioned in a domain of CD4 involved in TCR binding. In one embodiment, the antibody competes with Leu3A for binding to CD4 (Fishwild et al., Nat. Biotechnol. 14(7), 845-51 (1996)). A non-antibody CD4 binding peptide may also be capable of binding such epitope.

As used herein, specific binding to CD4 refers to the ability of the CD4 binding peptide, such as the anti-CD4 antibody or antigen binding fragment thereof, to bind to CD4, with an affinity of at least $1\times10^{-7}$ M, for instance with an affinity of at least $1\times10^{-8}$ M, such as $1\times10^{-9}$ M, for instance $1\times10^{-10}$ M.

The term "preferentially binding to CD4" refers herein to the property of the CD4 binding peptide, such as an anti-CD4 antibody or antigen binding fragment thereof, to bind to CD4 with above-mentioned affinity, wherein the affinity for CD4 is at least two-fold, such as at least 5-fold greater, for example at least 10-fold greater than its affinity for binding to a non-specific antigen (e.g., BSA, casein) other than CD4 or a polypeptide closely-related to CD4.

The term "selectively binding to CD4" refers herein to the property of the CD4 binding peptide, such as an anti-CD4 antibody or antigen binding fragment thereof, to bind to CD4 with above-mentioned affinity, wherein the affinity for CD4 is at least two-fold, such as at least 5-fold greater, for example at least 10-fold greater than its affinity for any other polypeptide.

The present invention relates to a CD4 binding peptide, such as an anti-CD4 antibody or antigen binding fragment thereof, capable of modulating at least one biological activity of CD4, for instance human CD4, such as an activity associated with cell cycle regulation. In one embodiment, the CD4 binding peptide, such as the anti-CD4 antibody or antigen binding fragment thereof, is capable of one or more of the activities mentioned in the section "Summary of the Invention" herein above.

In the present content by the term "modulating" is meant that a CD4 binding peptide, such as an anti-CD4 antibody or antigen binding fragment thereof, is capable of enhancing or diminishing biological activity of human CD4. In one embodiment, the invention features a CD4 binding peptide, such as an anti-CD4 antibody or antigen binding fragment thereof, which is capable of modulating at least one biological activity of CD4, such as inducing extension or arrest of cells in the G1 phase of the cell cycle. In one embodiment, the CD4 binding peptide, such as the anti-CD4 antibody or antigen binding fragment thereof, for use according to the present invention are capable of inducing extension or arrest of the G1 phase of the cell cycle. This may be determined by a method comprising the steps of
  1) contacting a population of CD4+ cells with the CD4 binding peptide;
  2) determining the number of cells in the G1 phase; and
  3) comparing said number with the number of cells in the G1 phase in a population, which has not been contacted with the CD4 binding peptide, wherein extension or arrest in G1 is defined as a number of cells in G1 in cell populations contacted with the CD4 binding peptide.

The number of cells in the G1 phase may be determined by a number of different methods, for example by staining DNA, wherein cells with a 2n DNA content are said to be in G1. It is also possible to determine the presence of one or more marker of G1, i.e. proteins or other compounds present primarily in the G1 phase of the cell cycle.

In one embodiment, the cells are tumor cells. In one embodiment, the tumor cells are cancer cells or haematological malignant cells. The cancer cells may be from either primary or metastatic cancer. In particular, the cells may be cells from any of the cancers described herein below in the section "clinical condition".

A CD4 binding peptide, such as an anti-CD4 antibody or antigen binding fragment thereof, for use according to invention may be capable of inducing phosphorylation of α-casein, as an exogenous $p56^{lck}$ substrate, by $p56^{lck}$. Induction of phosphorylation of α-casein may for example be determined by a method involving the following steps:
1) contacting a CD4+ cell with the CD4 binding peptide;
2) preparing a lysate of said cell;
3) contacting the lysate with α-casein;
4) determining phosphorylation of α-casein; and
5) comparing said phosphorylation with phosphorylation obtained using a lysate prepared from another cell, which has not been contacted with the CD4 binding peptide, wherein induction of phosphorylation is defined as a higher degree of phosphorylation obtained with lysates from cells contacted with the CD4 binding peptide.

The method may optionally further comprise the step of isolating CD4 as well as CD4 containing complexes from the lysate. This step may for instance be performed between steps 2 and 3. This may for example be accomplished by conventional immunoprecipitation techniques using antibodies to CD4. Such a step may ensure that only the activity of kinases associated with CD4 is determined.

Phosphorylation may be determined by any convention method, for example by use of phosphorylation specific antibodies or by use of radioactively labelled phosphates, for example from $^{32}P\gamma$-ATP.

One method for determining phosphorylation of α-casein is disclosed in example 2 herein below.

A CD4 binding peptide, such as an anti-CD4 antibody or antigen binding fragment thereof, for use according to the present invention may be capable of inducing $p56^{lck}$ autophosphorylation. Induction of $p56^{lck}$ autophosphorylation by a given CD4 binding peptide may be determined by a method involving the following steps:
1) contacting a CD4+ cell with the CD4 binding peptide;
2) preparing a lysate of said cell;
3) isolating complexes comprising $p56^{lck}$;
4) determining phosphorylation of $p56^{lck}$; and
5) comparing said phosphorylation with phosphorylation obtained using a lysate prepared from another cell, which has not been contacted with the CD4 binding peptide, wherein induction of phosphorylation is defined as a higher degree of phosphorylation obtained with lysates from cells contacted with the antibody.

Isolation of complexes comprising $p56^{lck}$ may be obtained by a number of different methods, for example by immunoprecipitation using antibodies specific to $p56^{lck}$ or a protein known to associate with $p56^{lck}$, for example antibodies to CD4. Phosphorylation may be determined as described above. One method for determining $p56^{lck}$ autophosphorylation is described in example 2 herein below.

A CD4 binding peptide, such as an anti-CD4 antibody or antigen binding fragment thereof, for use according to the present invention may be capable of increasing and/or upregulating p53 expression. Increase and/or upregulation of p53 expression by a given CD4 binding peptide may be determined by a method involving the following steps:
1) contacting a CD4+ cell with the CD4 binding peptide;
2) determining the expression of p53; and
3) comparing said expression with the expression of p53 in another cell, which has not been contacted with the CD4 binding peptide, wherein increase and/or upregulation of p53 expression is defined as a higher levels of p53 expression in cells contacted with the CD4 binding peptide.

The p53 expression may be determined by a number of conventional methods. This may for example be achieved using antibodies to p53, for example by Western blotting.

A CD4 binding peptide, such as an anti-CD4 antibody or antigen binding fragment thereof, for use according to the present invention may be capable of inducing phosphorylation of Dok-1 and/or SHIP-1 and/or SHIP-2. Induction of phosphorylation by a given CD4 binding peptide may be determined by a method involving the following steps:
1) contacting a CD4+ cell with the CD4 binding peptide;
2) preparing a lysate of said cell;
3) isolating complexes comprising Dok-1 and/or SHIP-1 and/or SHIP-2;
4) determining phosphorylation of Dok-1 and/or SHIP-1 and/or SHIP-2; and
5) comparing said phosphorylation with phosphorylation obtained using a lysate prepared from another cell, which has not been contacted with the CD4 binding peptide, wherein induction of phosphorylation is defined as a higher degree of phosphorylation obtained with lysates from cells contacted with the CD4 binding peptide.

Isolation of complexes comprising Dok-1 and/or SHIP-1 and/or SHIP-2 may be obtained by a number of different methods, for example by precipitation using a compound binding to Dok-1 and/or SHIP-1 and/or SHIP-2 or to proteins associated with Dok-1 and/or SHIP-1 and/or SHIP-2. Said compound may be antibodies. However, the compound may also be for example SH2. Phosphorylation may be determined as described above. On method for determining Dok-1 and/or SHIP-1 phosphorylation is described in example 2 herein below.

A CD4 binding peptide, such as an anti-CD4 antibody or antigen binding fragment thereof, for use according to the present invention may be capable increasing CD4+ cell, such as CD4+ T cell, for instance human CD4+ T cell sensitivity to radiation. This may be determined by a method comprising the steps of
1) contacting a CD4+ cell, such as a CD4+ T cell, for example a human CD4+ T cell with the CD4 binding peptide;
2) subjecting cells to radiation;
3) determining cell death, such as cell apoptosis; and
4) comparing said cell death with cell death obtained in cells, which has not been contacted with the CD4 binding peptide, wherein increase in sensitivity is defined as a higher degree of cell death, such as apoptosis in cells contacted with the CD4 binding peptide.

The radiation may be any radiation, such as UV. A large number of suitable methods for determining apoptosis are known to the skilled person. Non-limiting examples of suitable methods are the Annexin-V staining method, assays for caspase activity, staining for the presence of caspase cleavage products. Staining with 3,3'-dihexyloxacarbocyanine iodide or membrane integrity assays. Examples of methods for determining CD4+ cell sensitivity to radiation are described in examples 3, 4, 5 and 6 herein below.

A CD4 binding peptide, such as an anti-CD4 antibody or antigen binding fragment thereof, for use according to the invention may in one embodiment cause sequestration of p56$^{lck}$ away from the TCR. In addition, the CD4 binding peptide may directly generate a negative signal through p56$^{lck}$. Thus, a CD4 binding peptide for use according to the invention may often mediate its inhibitory effect on T-cell signaling via inhibition of signaling via the TCR, potentially via sequestration of p56$^{lck}$ away from the TCR, and also via direct inhibitory signaling. In one embodiment of the invention, the CD4 binding peptide may cause p56$^{lck}$ kinase activation, which in turn may lead to increased Dok-1 and/or SHIP-1 phosphorylation.

In one embodiment of the invention, the CD4 binding peptide is any of the anti-CD4-antibodies disclosed in patent application WO97/13852. For example, the antibody may be any of the murine antibodies capable of binding CD4 as described in said application, such as Leu 3a, RPA-TA, 92-09A-4F7-A5-2 or 92-09A-1D7-1-7-1. 92-09A-4f7-A5-2 and 92-09A-1D7-1-7-1 have been deposited with ATCC Patent Culture Depository under the Budapest Treaty under the deposition numbers HB 11307 and HB 11308, respectively. In one embodiment, the CD4 binding peptide is a human antibody, such as 2C11-8, 1F2, 1 E11, 2E4, 4D1, 6C1, 6G5, 7G2, 10C5, 1GI, 1G2, 2C5.1 or 4E4.2 as described in said application. In particular, the sequence of the VDJ junctions of 2C5.1 and 4E4.2 are described in said application. In one embodiment, the CD4 binding peptide is 6G5 as described in said application. The $V_H$ and $V_L$ sequences of 6G5 are given in FIG. 1.

In one embodiment of the invention the CD4 binding peptide is selected from the group consisting zanolimumab (GenMab, Denmark, also known as Humax-CD4 and HM6G (Fishwild et al., Clin Immunol. 92(2), 138-52 (1999) and the same as 6G5 as described in WO97/13852), keliximab (also known as IDEC-CE9.1, IDEC), clenoliximab (also known as IDEC-151, IDEC), TNX/355 (also known as Hu-5A8, Tanox, Biogen), TRX/1 (TolerRx/Genentech), IOT4a (also known as 13B8.2, Immunotech), priliximab (also known as cM-T412, Centocor) and 4162W94 (Glaxo). In some embodiments of the invention, the CD4 binding peptide is a humanized or a human antibody. Thus, in these embodiments the antibody may be selected from the group consisting of zanolimumab, TNX/355, TRX/1, IOT4a, and 4162W94. In one embodiment of the invention, the CD4 binding peptide is zanolimumab.

It is also comprised within the present invention that the CD4 binding peptide may be any antibody comprising at least the VDJ junction of the heavy and/or light chain or an antibody comprising for example at least the CDR3 of the heavy chain, or for instance at least all CDRs, such as at least one variable region, for instance both variable regions of an antibody selected from the group consisting of zanolimumab, keliximab, clenoliximab, TNX/355, TRX/1, IOT4a, priliximab and 4162W94 or the group consisting of Leu 3a, RPA-TA, 92-09A-4F7A5-2, 92-09A-1D7-1-7-1, 2C11-8, 1F2, 1E11, 2E4, 4D1, 6C1, 6G5, 7G2, 10C5, 1G1, 1G2, 2C5.1 and 4E4.2 disclosed in WO97/13852.

In one embodiment, the CD4 binding peptide for use according to the present invention is a CD4 binding peptide, such as an anti-CD4 antibody or antigen binding fragment thereof, capable of binding specifically to an epitope recognized by or overlapping with an epitope recognized by an antibody selected from the group consisting of zanolimumab, keliximab, clenoliximab, TNX/355, TRX/1, IOT4a, priliximab and 4162W94 or the group consisting of Leu 3a, RPA-TA, 92-09A-4F7A5-2, 92-09A-1D7-1-7-1, 2C11-8, 1F2, 1E11, 2E4, 4D1, 6C1, 6G5, 7G2, 10C5, 1G1, 1G2, 2C5.1 and 4E4.2 disclosed in WO97/13852.

Different assays available to the person skilled in the art may be used to determine whether a CD4 binding peptide, such as an anti-CD4 antibody or antigen binding fragment thereof, (also designated test CD4 binding peptide) recognizes the same or an overlapping epitope as a particular monoclonal antibody (also designated reference antibody). For instance, the assay involves the steps of:

providing CD4 or a fragment thereof comprising the epitope recognized by the reference antibody add the test CD4 binding peptide and the reference antibody to the said CD4, wherein either the test CD4 binding peptide or the reference antibody is labelled with a detectable label. Alternatively, both the test CD4 binding peptide and the reference antibody may be labelled with different detectable labels detecting the presence of the detectable label(s) at CD4 thereby detecting whether the test CD4 binding peptide is capable of displacing the reference antibody If the test CD4 binding peptide is capable of displacing the reference antibody, the test CD4 binding peptide recognizes the same or an overlapping epitope as the reference antibody. Thus if the reference antibody is labelled with a detectable label, then a low detectable signal at CD4 is indicative of displacement of the reference antibody. If the test CD4 binding peptide is labelled with a detectable label, then a high detectable signal at CD4 is indicative of displacement of the reference antibody. The CD4 fragment may for instance be immobilized on a solid support enabling facile handling. The detectable label may be any directly or indirectly detectable label, such as an enzyme, a radioactive isotope, a heavy metal, a colored compound or a fluorescent compound.

The CD4 binding peptides, such as the anti-CD4 antibodies or antigen binding fragments thereof, for use according to the present invention may be administered to patients by any method known in the medical arts for delivery of proteins and antibodies. Peptides, such as antibodies are particularly suited for parenteral administration. Parenteral administration may for example be by subcutaneous, intramuscular or intravenous administration, including infusion or injection. The pharmaceutical compositions of the present invention are suitable for administration using alternative drug delivery approaches as well (see for instance Langer, Science, 249, 1527-1533 (1990)).

Pharmaceutical compositions for parenteral administration usually comprise a solution of a CD4 binding peptide, such as a CD4 binding peptide, such as an anti-CD4 antibody or antigen binding fragment thereof, for instance a monoclonal antibody, dissolved in an acceptable carrier, such as an aqueous carrier. A variety of aqueous carriers can be used, for instance water, buffered water, 0.4% saline, 0.3% glycine and the like. These solutions are sterile and generally free of particulate matter. These compositions may be sterilized by conventional, well known sterilization techniques. These compositions may also be subjected to a virus reduction or multiple virus reductions by conventional well known techniques. The compositions may contain pharmaceutically acceptable auxiliary substances as required to approximate physiological conditions such as pH-adjusting and buffering agents, tonicity adjusting agents and the like, for example sodium acetate, sodium chloride, potassium chloride, calcium chloride, sodium lactate, etc. The concentration of CD4 binding peptide, such as an anti-CD4 antibody or antigen binding fragment thereof, in these formulations can vary widely, for example from less than about 0.5%, usually at or at least about 0.1% to as much as 1.5% or 2.0% or even more by weight and will be selected primarily based on fluid volumes, viscosities, etc., in accordance with the particular mode of administration selected. Actual methods for preparing parenterally administrable compositions will be known or apparent to those skilled in the art and are described in more detail in, for example, Remington's Pharmaceutical Sciences, 17th Ed., Mack Publishing Company, Easton, Pa. (1985), which is incorporated herein by reference.

Other useful formulations are such suitable for nasal and pulmonal administration, for instance inhalators and aerosols.

The CD4 binding peptides, such as an anti-CD4 antibodies or antigen binding fragments thereof, may be formulated as neutral or salt forms. Pharmaceutically acceptable salts include acid addition salts (formed with the free amino groups of the peptide compound) and which are formed with inorganic acids such as, for example, hydrochloric or phosphoric acids, or such organic acids as acetic acid, oxalic acid, tartaric acid, mandelic acid, and the like. Salts formed with the free carboxyl group may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

Injectables are usually prepared either as liquid solutions or suspensions, solid forms suitable for solution in, or suspension in, liquid such as sterile water prior to injection. The preparation may also be emulsified. The active ingredient is often mixed with excipients which are pharmaceutically acceptable and compatible with the active ingredient. Suitable excipients are, for example, water, saline, dextrose, glycerol, ethanol or the like, and combinations thereof. In addition, if desired, the preparation may contain minor amounts of auxiliary substances such as wetting or emulsifying agents, salts, pH buffering agents, or which enhance the effectiveness or transportation of the preparation.

The compositions containing a CD4 binding peptide, such as an anti-CD4 antibody or antigen binding fragment thereof, for use according to the present invention, or a cocktail thereof, may be administered for therapeutic treatment of a malignant disease, an inflammatory skin disease or for mediation of radiation treatment of a clinical condition. In therapeutic application, compositions are administered to a patient in an amount effective, at dosages and for periods of time necessary, to achieve a desired therapeutic result. In the context of the present invention, such an amount is defined as a "therapeutically effective amount." A therapeutically effective amount of a CD4 binding peptide, such as an anti-CD4 antibody or antigen binding fragment thereof, may vary according to factors such as the disease state, age, sex, and weight of the individual, and the ability of the CD4 binding peptide to elicit a desired response in the individual. A therapeutically effective amount is also one in which any toxic or detrimental effects of the CD4 binding peptide, such as the anti-CD4 antibody or antigen binding fragment thereof, are outweighed by the therapeutically beneficial effects.

Therapeutically effective amounts of CD4 binding peptides for use according to the present invention may be determined by clinicians, as it is known in the art. For instance, for topical or local use, the amount of CD4 binding peptide may be lower than for single systemic therapy, whereby the potential systemic side effects (such as systemic depletion of $CD4^+$ cells) may be diminished or avoided. Dosages may for instance to in the range of 20 mg to 2000 mg, such as for instance in the range of 20 mg to 100 mg (such as for instance in an amount of about 20 mg, about 40 mg, about 60 mg, about 80 mg or about 100 mg), or for instance in an amount of about 150 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, about 1000 mg, about 1050 mg, about 1100 mg, about 1150 mg, about 1200 mg, about 1250 mg, about 1300 mg, about 1350 mg, about 1400 mg, about 1450 mg, about 1500 mg, about 1550 mg, about 1600 mg, about 1650 mg, about 1700 mg, about 1750 mg, about 1800 mg, about 1850 mg, about 1900 mg, about 1950 mg, or about 2000 mg. Generally, the clinician will be able to determine a suitable dosage through common experimentation designed to establish a suitable therapeutic dosage as it is well known in the art.

For some embodiments, the CD4 binding peptide, such as an anti-CD4 antibody or antigen binding fragment thereof, is administered locally, for example by direct injection to the disease site. In other embodiments, the CD4 binding peptide, such as the anti-CD4 antibody or antigen binding fragment thereof, is administered in a systemic manner.

Some of the CD4 binding peptides for use in the present invention are sufficiently active, but for some of the others, the effect will be enhanced if the preparation further comprises pharmaceutically acceptable additives and/or carriers. Such additives and carriers will be known in the art. In some cases, it will be advantageous to include a compound, which promotes delivery of the active substance to its target.

In one embodiment of the invention, a CD4 binding peptide, such as an anti-CD4 antibody or antigen binding fragment thereof, is administered at least once prior to radiation treatment, and antibody is administered at least once a week.

In one embodiment of the invention, a CD4 binding peptide, such as an anti-CD4 antibody or antigen binding fragment thereof, is administered two, three, four, five or even more times prior to radiation treatment, and antibody is administered at least once a week.

In one embodiment of the invention, a CD4 binding peptide, such as an anti-CD4 antibody or antigen binding fragment thereof, is administered at the same time as radiation treatment is initiated.

In one embodiment of the invention, a CD4 binding peptide, such as an anti-CD4 antibody or antigen binding fragment thereof, is administered one, two, three, four, five or even more times after initiation of radiation treatment, and antibody is administered at least once a week.

In one embodiment of the invention, the period of administration of said CD4 binding peptide in such duration as will be therapeutically effective. The duration of administration depends on the subject to be treated, including, for instance the weight and age of the subject, the disease to be treated and the stage of disease. The period of CD4 binding peptide administration may be in the range of 1 to 48 weeks, such as in the range of 4 to 30 weeks, or for instance in the range of 8 to 16 weeks, such as 12 weeks.

In one embodiment of the invention, the administration of the CD4 binding peptide may be repeated several times, in such a manner that will be therapeutically effective. The time between two consecutive treatments may be in the range of 1 to 200 weeks, such as in the range of 4 to 104 weeks, for instance in the range of 24 weeks to 52 weeks.

In one embodiment, the present invention relates to use of radiation treatment in combination with administration of a CD4 binding peptide, such as an anti-CD4 antibody or antigen binding fragment thereof, for treatment of a clinical condition, such as any of the clinical conditions described herein above, including malignant or inflammatory skin diseases. A number of radiation treatments may be used, such as psoralen and long-wave ultraviolet radiation (PUVA), UVB, narrow band UVB, high dose UVA, photopheresis, electron beam, or x-ray. In one embodiment, the present invention relates to psoralen and long-wave ultraviolet radiation (PUVA).

In one embodiment of the invention, PUVA is used as the radiation treatment. Psoralen compounds are administered orally or topically as described above. Oral administration of said psoralen may take place as described above, such as at least about one hour prior to the ultraviolet A (UVA) radiation treatment and no more than about three hours prior to said radiation treatment. When psoralen is applied directly to the skin, ultraviolet A (UVA) radiation treatment may take place as described above, for instance within the range of 1 to 30 minutes, such as within 1 to 15 minutes. PUVA treatment is given as 1 to 10 treatments per month, such as 1 to 7 treatments per months, for instance 1 to 5 treatments per months, such as 1 to 5 weekly treatments, for instance 1 to 3 weekly treatments, such as 1 weekly treatment. In one embodiment, the radiation treatment is given in the same treatment interval as the administration of the CD4 binding peptide.

The light intensity during the PUVA radiation treatment according to the present invention will be carried out with attention paid to controlling the maximum radiant exposure so as to avoid unnecessary injury to the patient. The skilled person will readily be able to determine a suitable light intensity. Methods for calculating maximum radiant exposure to ultraviolet light are known in the art. The PUVA radiation treatment will be carried out using long wavelength ultraviolet light (UVA) at a wavelength of for instance in the range of 280 to 440 nm, such as in the range of 320 to 400 nm.

The duration of the initial UVA radiation treatment according to the present invention may be in the range of 10 seconds to 20 minutes, for instance in the range of 20 seconds to 10 minutes. The exposure time may gradually increase from treatment to treatment. In general, exposure time to UVA may be in the range of 1 to 60 minutes, for instance in the range of 1 to 30 minutes.

Psoralen is defined as any of a number of drugs and other substances that binds to the DNA in cells and stops them from multiplying and is a photosensitizing chemical increasing the skin's reaction to light for a therapeutic effect. Psoralens are compounds comprising a planar tricyclic structure which have a natural affinity for nucleic acids and may intercalate between bases, getting between the two strands of the DNA double helix, typically between adenine and thymine bases. Upon irradiation with long wave ultraviolet (UV) light, psoralens typically become covalently attached to the nucleic acids, often to thymidines, and also to uridines and cytidines, effectively tying the double helix together. Processes that require the unwinding of the double helix may then be inhibited by the psoralen molecules. Psoralen preferably stops the activities of the cells without killing the cells.

In one embodiment, a psoralen compound for use according to the present invention is of the general formula of:

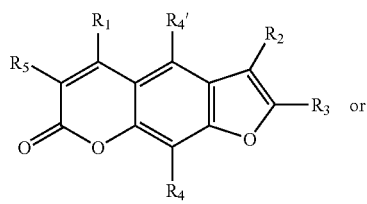 or

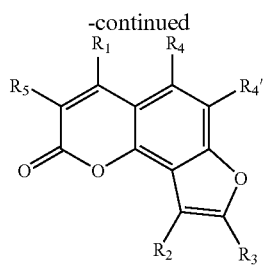

wherein $R_1$, $R_2$, $R_3$, $R_4$, $R_4'$ and $R_5$ individually are selected from the group consisting of hydrogen, halogen, $C_{(1-10)}$-alkyl, and $C_{(1-10)}$-alkyl substituted with halogen, amine or hydroxyl, and $C_{(1-10)}$-ethers optionally substituted with hydroxy; or $R_1$ and $R_5$ together form a pyrido.

Halogen should be taken to mean a halogen radical selected from the group consisting of chlorine, fluorine, bromine and iodine.

$C_{(1-10)}$-alkyl should be taken to mean an alkyl radical containing from 1 to 10 carbon atoms. The alkyl radical may be straight or branched. Examples of $C_{(1-10)}$-alkyls are methyl, ethyl, propyl, isopropyl, butyl, isobutyl and pentyl.

Amine should be taken to mean a radical of the structural formula $R_a R_b N$—, wherein $R_a$ and $R_b$ independently are hydrogen or a $C_{(1-10)}$-alkyl. In one embodiment, $R_a$ and $R_b$ are both hydrogen.

Hydroxy should be taken to mean a radical of the structural formula HO—.

$C_{(1-10)}$-alkyl-O— should be taken to mean an ether radical containing from 1 to 10 carbon atoms. The ether radical may be straight or branched. Examples of $C_{(1-10)}$-alkyl-O— are methoxy, ethoxy, propoxy, isopropoxy, butoxy, isobutoxy and pentoxy.

In one embodiment, the psoralen compound may be selected from the group consisting of pyrido-[3,4-c]psoralen, 7-methylpyrido-[3,4-c]psoralen, 5-methoxypsoralen, 8-methoxypsoralen, 4,5',8-trimethylpsoralen, 4-methylpsoralen, 4,4-dimethylpsoralen, 4-5'-dimethylpsoralen, 4', 8-methoxypsoralen, 4'-(omega-amino-2-oxa)alkyl-4,5',8-trimethylpsoralen, 4'-(4-amino-2-oxa)-butyl-4,5',8-trimethylpsoralen, 4'-chloromethyl-4,5',8-trimethylpsoralen, 4'-aminomethyl-4,5',8-trimethylpsoralen, 4'-(2-hydroxyethoxy)-methyl-4,5',8-trimethylpsoralen, 4'-(6-hydroxyhexyloxy)-methyl-4,5',8-trimethylpsoralen, 4'-hydroxymethyl-4,5',8-trimethylpsoralen, 5-methyl-angelicin and 2H-furo[2,3-h][1]benzopyran-2-one.

In one embodiment, the psoralen may be 5-methoxypsoralen or 8-methoxypsoralen. 5-methoxypsoralen is for example available with the trade name Pentaderm, and 8-methoxypsoralen is for example available with the trade name Genoxalen.

The psoralens for use in the present invention may be administered to patients by any method known in the medical arts for delivery of psoralens. Psoralens are in general suited for oral or topical administration.

The formulations comprising psoralen may be prepared by conventional techniques, for instance as described in Remington: The Science and Practice of Pharmacy 1995, edited by E. W. Martin, Mack Publishing Company, 19th edition, Easton, Pa. The pharmaceutical formulation may have any form known to the person skilled in the art. For example, the pharmaceutical formulation may be in the form of a bioadhesive and non-bioadhesive gel, powder, tablets, lozenges, chewing tablets, chewing gum, pills, capsules, cachets, suppositories, dispersible granules, patches, a lollipop, ointment, lotion, cream, foam, implant or balm. Pharmaceutical formulations comprising psoralen are usually in a form selected from a group consisting of tablets, capsules, crèmes, lotions, gels or ointments.

The formulation comprising psoralens usually comprises pharmaceutically acceptable excipients. Such pharmaceutically acceptable excipients are not necessarily therapeutically active ingredients, but rather said excipients may be one or more substances which may act as diluents, flavoring agents, solubilisers, lubricants, suspending agents, binders, preservatives, wetting agents, tablet disintegrating agents, or an encapsulating material. Such excipients include not are not limited to pharmaceutical grades of mannitol, lactose, starch, magnesium stearate, sodium saccharine, talcum, cellulose, glucose, lactose, pectin, dextrin, starch, gelatin, sucrose, magnesium carbonate, tragacanth, methylcellulose, sodium carboxymethylcellulose, a low melting wax, cocoa butter, and the like. In addition, the pharmaceutical acceptable excipients may be colorants, flavors, stabilizers, buffers, artificial and natural sweeteners, dispersants, thickeners and the like.

In powders, the excipient may be a finely divided solid, which is a mixture with the finely divided active components. In tablets, the active components are mixed with the excipient having the necessary binding capacity in suitable proportions and compacted in the shape and size desired. The powders and tablets may contain from one to about seventy percent of the active compound.

Creams, ointments or gels according to the present invention are semi-solid formulations of the active ingredient for external application. They may be made by mixing the active ingredient in finely divided or powdered form, alone or in solution or suspension in an aqueous or non-aqueous fluid, with the aid of suitable machinery, with a greasy or non-greasy base, such as known to the person skilled in the art.

Examples of bases are bases that may comprise one or more hydrocarbons such as hard, soft or liquid paraffin, glycerol, paraffin oil, beeswax, a metallic soap; a mucilage; an oil of natural origin such as almond, corn, arachis, castor or olive oil or derivatives thereof such as castor oil polyoxyl; wool fat or its derivatives or a fatty acid and/or ester such as steric or oleic acid, or isopropyl myristate.

The base may furthermore comprise an alcohol such as propylene glycol, polyethylene glycol (PEG) of different molecular weights, cetyl alcohol, ethanol or a macrogel. The formulation may incorporate any suitable surface active agent or emulsifier such as an anionic, cationic or non-ionic surfactant such as a sorbitan ester, polysorbate, Cremophor EL, Tween 20, or a polyoxyethylene derivative thereof. Suspending agents such as natural gums, cellulose derivatives or inorganic materials such as silicaceous silicas, and other ingredients such as lanolin, may also be included.

Lotions according to the present invention include those suitable for application to the skin or eye. Lotions or liniments for application to the skin may include an agent to hasten drying and to cool the skin, such as an alcohol or acetone, and/or a moisturizer such as glycerol or an oil such as castor oil or arachis oil.

In one embodiment of the invention, the unit dosage of psoralen may be in the range of from about 1 to about 1000 mg, for instance from about 2 to from about 500 mg, such as from about 5 to about 100 mg, for instance from about 10 to about 50 mg.

When administered orally, the psoralen may for instance be administered at least 15 min, such as at least 30 min, for example at least one hour, such as at least 2 hours prior to radiation treatment. The psoralen is administered at the most 2 days, such as at the most 1 day, for instance at the most 12 hours, such as at the most 6 hours, for instance at the most 3 hours, such as at the most 2 hours prior to radiation treatment. In one embodiment, the psoralen is administered about one hour prior to the radiation treatment and no more than about three hours prior to the radiation treatment. When administered directly on the skin, psoralen may be applied within 1 min to 2 days, for instance within 1 min. to 1 day, such as within 1 min to 12 hours, for instance within 1 min to 6 hours, such as within 1 min. to 3 hours, for instance within 1 min. to 1 hour, such as within 1 to 30 minutes prior to UV radiation treatment, for instance ultraviolet A (UVA) radiation treatment, such as within 1 to 15 minutes prior said radiation treatment.

In one embodiment of the invention, UVB or UVB narrow band radiation treatment may be given. UVB or UVB narrow band treatment is given as 1 to 10 treatments per month, such as 1 to 7 treatments per months, for instance 1 to 5 treatments per months, such as 1 to 5 weekly treatments, for instance 1 to 3 weekly treatments, such as 1 weekly treatment. In one embodiment, the radiation treatment is given in the same treatment interval as the administration of the CD4 binding peptide. The light intensity is adjusted according to standard regimens, most often based on minimal erythema dose (MED) or standard erythema dose (SED). MED is defined as the minimum amount of x-rays or other form of radiation sufficient to produce redness of the skin after application, regarded as the dose that is safe to give at one time. The wavelength used for UVB or UVB narrow band may be in the range of 250 to 400 nm, such as in the range of 280 to 320 nm.

The term "electron beam radiation treatment" is used herein interchangeably with the term "Total skin electron beam therapy (TSEBT)".

In one embodiment of the invention, electron beam radiation treatment may be used as the radiation treatment. Electron beam may be applied to localized or total skin and are delivered at an energy of in the range of 1 to 15 MeV, such as in the range of 4 to 9 MeV to treat the skin only. The dose for a course of total skin electron beam therapy (TSEBT) is often up to 36 Gy which may be delivered in fractionate dosages of normally in the range of 0.1 to 5 Gy, such as in the range of 1.5 to 2 Gy, up to three times weekly in the same treatment interval as the administration of the CD4 binding peptide.

In one embodiment of the invention, the radiation treatment may be photopheresis. Photopheresis is performed by leukapheresis with isolation of the mononuclear fraction, which is then exposed to UVA and Genoxalen or any other psoralen as described herein above. The irradiated cells are then returned to the patient. The method described above is well known to those skilled in the art. Photopheresis is particularly suited for malignant conditions involving circulating malignant cells, such as T cell lymphomas, such as for instance CTCL. Photopheresis is initially conducted on at least 2 consecutive days, such as 2 consecutive days once a month or for instance twice a month, until maximal clearing has occurred. This is followed by at least 3 months, such as 6 months of monthly treatment and then gradually tapered to 4-weeks intervals, such as 6-weeks intervals, for instance 8-weeks intervals and discontinuation. However, the person skilled in the art is capable of adjusting the particular photopheresis treatment in accordance with the patient, the condition to be treated and own experience.

In one embodiment of the invention, X-rays may be used as the radiation treatment. X-rays may be given to lymphomas localized to lymphnodes, visceral organs, lesions in the skin such as tumors or extensive large-plaque disease. The treatment may for instance be administered after administration of the CD4 binding peptide, in the same treatment interval as the administration of the CD4 binding peptide. The type of radiation that may be used for the present invention includes, but is not limited to, low voltage X-ray. Fractionating of dose is often implemented. Methods to determine the intensity and duration of the x-rays necessary to achieve therapeutic efficiency in patients in need of the treatment are well known to those skilled in the art.

The present invention relates to treatment of clinical condition with a CD4 binding peptide, such as an anti-CD4 antibody or antigen binding fragment thereof, and radiation. The clinical condition may be any clinical condition responsive to such a treatment.

In one embodiment, the clinical condition is a condition involving directly or indirectly cells expressing CD4. Thus, the clinical condition may be any condition involving directly or indirectly CD4+ T-cells. Thus, the clinical condition may be a disease involving increased proliferation of CD4+ T-cells, such as hyperproliferation of CD4+ T-cells, or it may involve increased recruitment of CD4+ T-cells to a diseased site, for instance undesirable recruitment of CD4+ T-cells to a diseased site. Clinical conditions involving hyperproliferation of CD4+ T-cells include for instance certain malignant diseases.

In one embodiment, the clinical condition may be at least partly responsive to radiation treatment.

In one embodiment, the clinical condition is selected from the group consisting of malignant diseases and inflammatory skin diseases.

The malignant disease may be any malignant disease, for instance primary cancer or metastatic cancer. The term "malignant disease" as used herein is meant to cover also pre-malignant diseases.

By "primary cancer" is meant a group of tumor cells, which have acquired at least one characteristic feature of cancer cells, however have not yet invaded the neighboring tissues and hold together in a tumor localized at the place of primary origin. By "metastatic cancer" is meant a group of tumor cells, which originate from the cells of a primary cancer, which have invaded the tissue surrounding said primary cancer, disseminated through the body, adhered at a new distant place and grown to a new tumor.

Pre-malignant and/or malignant conditions may for example be cancer or conditions which may develop into a cancer. The term cancer within the scope of the present invention covers both malignant and benign tumors, as well as leukaemia and lymphoma.

Cancer may for example be adenomas, carcinomas or sarcomas. Cancer may for example be selected from the group consisting of melanoma, brain tumors, neuroblastomas, breast cancer, lung cancer, prostate cancer, cervix cancer, uterine cancer, ovarian cancer, leukaemia, colon cancer, rectum cancer, cancer of the testis, cancer of the kidney, cancer of the liver, cancer of the lip, cancer of the tongue, cancer of the stomach, skin cancer, sarcomas, mesotheliomas, bladder cancer, bone tumors, malignant pleural effusions, ascites, meningeal carcinomatosis, head and neck cancers and cancers of endocrine organs such as: thyroid gland, pituitary gland and suprarenal gland.

In one embodiment said malignant disease is selected from a group consisting adult T-cell leukaemia or lymphoma and T-cell prolymphocytic leukaemia In one embodiment said malignant disease is selected form a group consisting of CD4+ cutaneous T-cell lymphomas, such as mycosis fungoides, Sezary syndrome, lymphoid papulosis or anaplastic large cell lymphoma.

In one embodiment said malignant disease is selected form a group consisting of CD4+ nodal T-cell lymphomas, such as peripheral T-cell lymphoma, angioimmunoblastic T-cell lymphoma or anaplastic large T-cell lymphoma.

In one embodiment, the inflammatory disease of the skin is selected from the group consisting of psoriasis, dermatitis eczema, atopic dermatitis, scleroderma, lichen planus and alopecia areata.

The following is a list of embodiments of the present invention:

Embodiment 1: Use of a CD4 binding peptide in the preparation of a pharmaceutical composition for the treatment of a clinical condition in an individual who receives or will receive radiation treatment.

Embodiment 2: Use of a CD4 binding peptide in the preparation of a pharmaceutical composition for the treatment of a clinical condition in combination with radiation treatment.

Embodiment 3: Use of a CD4 binding peptide in the preparation of a pharmaceutical composition for the mediation of radiation treatment of a clinical condition.

Embodiment 4: Use of a CD4 binding peptide and a psoralen compound in the preparation of a pharmaceutical kit of parts for the treatment of a clinical condition.

Embodiment 5 Use according to embodiment 4, wherein the pharmaceutical kit of parts is for mediation of radiation treatment.

Embodiment 6: Use according to any of embodiments 1 to 5, wherein the CD4 binding peptide is capable of binding to human CD4.

Embodiment 7: Use according to any of embodiments 1 to 6, wherein the CD4 binding peptide is manufactured using mammalian cell culture.

Embodiment 8: Use according to any of embodiments 1 to 7, wherein the CD4 binding peptide is capable of activating the $p56^{lck}$ kinase.

Embodiment 9: Use according to embodiment 8, wherein the activation of $p56^{lck}$ kinase increases the phosphorylation of at least one of the inhibitory adaptor molecules, Dok-1 and/or SHIP-1.

Embodiment 10: Use according to any of embodiments 1 to 9, wherein the CD4 binding peptide is an anti-CD4 antibody or a CD4 binding fragment thereof.

Embodiment 11: Use according to embodiment 10, wherein the antibody is a monoclonal antibody.

Embodiment 12: Use according to embodiment 10 or embodiment 11, wherein the antibody is a humanized antibody.

Embodiment 13: Use according to any of embodiments 10 to 11, wherein the antibody is a human antibody.

Embodiment 14: Use according to any of embodiments 10 to 13, wherein the antibody has a light chain of the kappa-type (κ).

Embodiment 15: Use according to any of embodiments 10 to 14, wherein the antibody is selected from the group consisting of zanolimumab, keliximab, clenoliximab, TNX/355, TRX/1, IOT4a, priliximab, and 4162W94.

Embodiment 16: Use according to embodiment 15, wherein the antibody is zanolimumab.

Embodiment 17: Use according to any of embodiments 1 to 16, wherein the radiation treatment is selected from the group consisting of a combination of administration of a psoralen compound and long-wave ultraviolet radiation (PUVA); UVB; narrow band UVB; high dose UVA; electron beam; and x-ray.

Embodiment 18: Use according to embodiment 17, wherein the radiation treatment is a combination of administration of a psoralen compound and long-wave ultraviolet radiation (PUVA).

Embodiment 19: Use according to embodiment 18, wherein the psoralen compound has the general formula:

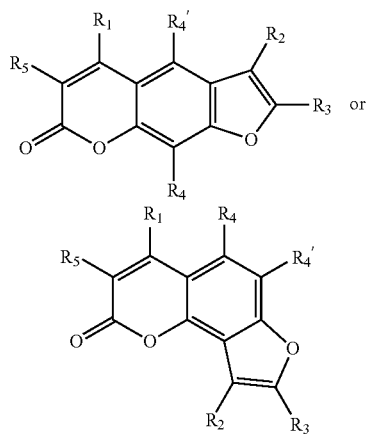

wherein $R_1$, $R_2$, $R_3$, $R_4$, $R_4'$ and $R_5$ individually are selected from the group consisting of hydrogen, halogen, $C_{(1-10)}$-alkyl, and $C_{(1-10)}$-alkyl substituted with halogen, amine or hydroxyl, and $C_{(1-10)}$-ethers optionally substituted with hydroxy; or $R_1$ and $R_5$ together form a pyrido.

Embodiment 20: Use according to any of embodiments 1 to 19, wherein the psoralen compound is selected from the group consisting of pyrido-[3,4-c]psoralen, 7-methylpyrido-[3,4-c]psoralen, 5-methoxypsoralen, 8-methoxypsoralen, 4,5',8-trimethylpsoralen, 4-methylpsoralen, 4,4-dimethylpsoralen, 4-5'-dimethyl-psoralen, 4', 8-methoxypsoralen, 4'-(omega-amino-2-oxa)alkyl-4,5',8-trimethylpsoralen, 4'-(4-amino-2-oxa)-butyl-4,5',8-trimethylpsoralen, 4'-chloromethyl-4,5',8-trimethylpsoralen, 4'-aminomethyl-4,5',8-trimethylpsoralen, 4'-(2-hydroxyethoxy)-methyl-4,5',8-trimethylpsoralen, 4'-(6-hydroxyhexyloxy)-methyl-4,5',8-trimethylpsoralen, 4'-hydroxymethyl-4,5',8-trimethylpsoralen, 5-methyl-angelicin and 2H-furo[2,3-h][1] benzopyran-2-one.

Embodiment 21: Use according to embodiment 20, wherein the psoralen compound is 5-methoxypsoralen or 8-methoxypsoralen.

Embodiment 22: Use according to any of embodiments 1 to 21, wherein the clinical condition is a malignant disease or an inflammatory skin disease.

Embodiment 23: Use according to embodiment 22, wherein the clinical condition is a malignant disease.

Embodiment 24: Use according to embodiment 22 or embodiment 23, wherein the malignant disease is selected from the group consisting of leukaemia and lymphoma.

Embodiment 25: Use according to any of embodiments 22 to 24, wherein the malignant disease is T-cell prolymphocytic leukaemia.

Embodiment 26: Use according to any of embodiments 22 to 24, wherein the malignant disease is selected from the group consisting of CD4+ cutaneous T-cell lymphomas.

Embodiment 27: Use according to embodiment 26, wherein the malignant disease is selected from the group consisting of mycosis fungoides, Sezary syndrome, lymphoid papulosis and anaplastic large cell lymphoma.

Embodiment 28: Use according to any of embodiments 22 to 24, wherein the malignant disease is selected from the group consisting of CD4+ nodal T-cell lymphomas.

Embodiment 29: Use according to embodiment 28, wherein the malignant disease is selected from the group consisting of peripheral T-cell lymphoma, angioimmunoblastic T-cell lymphoma and anaplastic large T-cell lymphoma.

Embodiment 30: Use according to embodiment 22, wherein the clinical condition is an inflammatory skin disease.

Embodiment 31: Use according to embodiment 22 or embodiment 30, wherein the inflammatory skin disease is selected from the group consisting of psoriasis, dermatitis eczema, atopic dermatitis, scleroderma, lichen planus and alopecia areata.

Embodiment 32: A method of treatment of a malignant disease comprising administering to a subject in need thereof a therapeutically effective amount of a CD4 binding peptide and subjecting said subject to radiation treatment.

Embodiment 33: A method according to embodiment 32, wherein the malignant disease is selected from the group consisting of leukaemia and lymphoma.

Embodiment 34: A method according to embodiment 32 or embodiment 33, wherein the malignant disease is T-cell prolymphocytic leukaemia.

Embodiment 35: A method according to embodiment 32 or embodiment 33, wherein the malignant disease is selected from the group consisting of CD4+ cutaneous T-cell lymphomas.

Embodiment 36: A method according to embodiment 35, wherein the malignant disease is selected from the group consisting of mycosis fungoides, Sezary syndrome, lymphoid papulosis and anaplastic large cell lymphoma.

Embodiment 37: A method according to embodiment 32 or embodiment 33, wherein the malignant disease is selected from the group consisting of CD4 positive nodal T-cell lymphomas.

Embodiment 38: A method according to embodiment 37, wherein the malignant disease is selected from the group consisting of peripheral T-cell lymphoma, angioimmunoblastic T-cell lymphoma and anaplastic large T-cell lymphoma.

Embodiment 39: A method of treatment of an inflammatory skin disease comprising administering to a subject in need thereof a therapeutically effective amount of a CD4 binding peptide and subjecting said subject to radiation treatment.

Embodiment 40: A method according to embodiment 39, wherein the inflammatory skin disease is selected from a group consisting of psoriasis, dermatitis eczema, atopic dermatitis, scleroderma, lichen planus and alopecia areata.

Embodiment 41: A method of mediating radiation treatment of a clinical condition comprising administering to a subject in need thereof a therapeutically effective amount of a CD4 binding peptide and subjecting said subject to radiation treatment.

Embodiment 42: A method according to any of embodiments 32 to 41, wherein the CD4 binding peptide is capable of binding to human CD4.

Embodiment 43: A method according to any of embodiments 32 to 42, wherein the CD4 binding peptide is manufactured using mammalian cell culture.

Embodiment 44: A method according to any of embodiments 32 to 43, wherein the CD4 binding peptide is capable of activating the $p56^{Ick}$ kinase.

Embodiment 45: A method according to embodiment 44, wherein the activation of p56$^{lck}$ kinase increases the phosphorylation of at least one of the inhibitory adaptor molecules, Dok-1 and/or SHIP-1.

Embodiment 46: A method according to any of embodiments 32 to 45, wherein the CD4 binding peptide is an anti-CD4 antibody or a CD4 binding fragment thereof.

Embodiment 47: A method according to embodiment 46, wherein the antibody is a monoclonal antibody.

Embodiment 48: A method according to embodiment 46 or embodiment 47, wherein the antibody is a humanized antibody.

Embodiment 49: A method according to embodiment 46 or embodiment 47, wherein the antibody is a human antibody.

Embodiment 50: A method according to any of embodiments 46 to 49, wherein the antibody has a light chain of the kappa-type (κ).

Embodiment 51: A method according to any of embodiments 46 to 50, wherein the antibody is selected from the group consisting of zanolimumab, keliximab, clenoliximab, TNX/355, TRX/1, IOT4a, priliximab, and 4162W94.

Embodiment 52: A method according to embodiment 51, wherein the antibody is zanolimumab.

Embodiment 53: A method according to any of embodiments 32 to 52, wherein the radiation treatment is selected from the group consisting of psoralen and long-wave ultraviolet radiation (PUVA); UVB; narrow band UVB; high dose UVA; electron beam; and x-ray.

Embodiment 54: A method according to embodiment 53, wherein the radiation treatment is psoralen and long-wave ultraviolet radiation (PUVA), and wherein a psoralen compound is administered prior to UVA treatment.

Embodiment 55: A method according to embodiment 54, wherein the psoralen compound has a general formula:

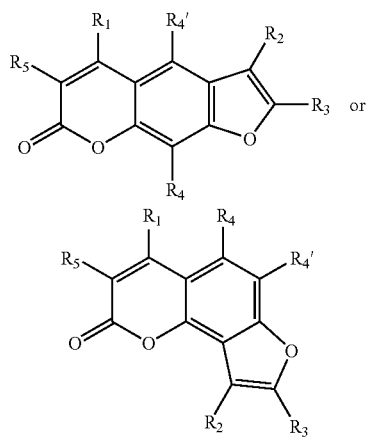

wherein $R_1$, $R_2$, $R_3$, $R_4$, $R_4'$ and $R_5$ individually are selected from the group consisting of hydrogen, halogen, $C_{(1-10)}$-alkyl, and $C_{(1-10)}$-alkyl substituted with halogen, amine or hydroxyl, and $C_{(1-10)}$-ethers optionally substituted with hydroxy; or $R_1$ and $R_5$ together form a pyrido.

Embodiment 56: A method according to any of embodiments 32 to 55, wherein the psoralen compound is selected from the group consisting of pyrido-[3,4-c]psoralen, 7-methylpyrido-[3,4-c]psoralen, 5-methoxypsoralen, 8-methoxypsoralen, 4,5',8-trimethylpsoralen, 4-methylpsoralen, 4,4-dimethylpsoralen, 4-5'-dimethylpsoralen, 4',8-methoxypsoralen, 4'-(omega-amino-2-oxa)alkyl-4,5',8-trimethylpsoralen, 4'-(4-amino-2-oxa)-butyl-4,5',8-trimethylpsoralen, 4'-chloromethyl-4,5',8-trimethylpsoralen, 4'-aminomethyl-4,5',8-trimethylpsoralen, 4'-(2-hydroxyethoxy)-methyl-4,5',8-trimethylpsoralen, 4'-(6-hydroxyhexyloxy)-methyl-4,5',8-trimethylpsoralen, 4'-hydroxymethyl-4,5',8-trimethylpsoralen, 5-methyl-angelicin and 2H-furo[2,3-h][1]benzopyran-2-one.

Embodiment 57: A method according to embodiment 56, wherein the psoralen compound is 5-methoxypsoralen or 8-methoxypsoralen.

Embodiment 58: A method according to any of embodiments 54 to 57, wherein the psoralen compound is administered in a period of from 5 to 0.5 hours before the radiation treatment.

Embodiment 59: A method according to embodiment 58, wherein the psoralen compound is administered in a period of from 2 to 1 hours before the radiation treatment.

Embodiment 60: A method according to any of embodiments 32 to 59, wherein the CD4 binding peptide is administered by intravenous, subcutaneous or intramuscular injection.

Embodiment 61: A method according to any of embodiments 32 to 60, wherein the CD4 binding peptide is administered at least once prior to radiation treatment.

Embodiment 62: A method according to any of embodiments 32 to 61, wherein the CD4 binding peptide is administered once a week.

Embodiment 63: A method according to any of embodiments 32 to 62, wherein said subjects are subjected to radiation treatment in the range of 1 to 5 times weekly.

Embodiment 64: A method according to any of embodiments 32 to 63, wherein at least one CD4 binding peptide treatment and at least one radiation treatment is given within the same week.

Embodiment 65: A method according to any of embodiments 32 to 64, wherein the CD4 binding peptide treatment and the radiation treatment are given within a period of from 4 to 30 weeks.

Embodiment 66: A method according to embodiment 65, wherein the CD4 binding peptide treatment and the radiation treatment are given within a period of from 8 to 16 weeks.

Embodiment 67: A method according to embodiment 66, wherein the CD4 binding peptide treatment and the radiation treatment are given within a period of 12 weeks.

Embodiment 68: A method according to any of embodiments 32 to 67, wherein the radiation treatment is given locally or to total skin.

Embodiment 69: A method according to any of embodiments 32 to 67, wherein the radiation treatment is given to extracorporeal blood.

Embodiment 70: A method according to embodiment 69, wherein the radiation treatment is photopheresis.

Embodiment 71: A kit of parts comprising a CD4 binding peptide and a psoralen compound together with one or more pharmaceutically acceptable excipients for use as a medicament.

Embodiment 72: A kit of parts comprising a CD4 binding peptide and a psoralen compound together with one or more pharmaceutically acceptable excipients for use as a medicament in the treatment of a malignant disease.

Embodiment 73: A kit of parts comprising a CD4 binding peptide capable of binding to CD4 and a psoralen compound together with one or more pharmaceutically acceptable excipients for use as a medicament in the treatment of a malignant disease in combination with radiation treatment.

Embodiment 74: A kit of parts according to embodiment 72 or 73, wherein the malignant disease is selected from the group consisting of leukaemia and lymphoma.

Embodiment 75: Use according to any of embodiments 72 to 74, wherein the malignant disease is T-cell prolymphocytic leukaemia.

Embodiment 76: Use according to any of embodiments 72 to 74, wherein the malignant disease is selected from the group consisting of CD4+ cutaneous T-cell lymphomas.

Embodiment 77: Use according to embodiment 76, wherein the malignant disease is selected from the group consisting of mycosis fungoides, Sezary syndrome, lymphoid papulosis and anaplastic large cell lymphoma.

Embodiment 78: Use according to any of embodiments 72 to 74, wherein the malignant disease is selected from the group consisting of CD4+ nodal T-cell lymphomas.

Embodiment 79: Use according to embodiment 78, wherein the malignant disease is selected from the group consisting of peripheral T-cell lymphoma, angioimmunoblastic T-cell lymphoma and anaplastic large T-cell lymphoma.

Embodiment 80: A kit of parts comprising a CD4 binding peptide and a psoralen compound together with one or more pharmaceutically acceptable excipients for use as a medicament in the treatment of an inflammatory skin disease.

Embodiment 81: A kit of parts comprising a CD4 binding peptide and a psoralen compound together with one or more pharmaceutically acceptable excipients for use as a medicament in the treatment of an inflammatory skin disease in combination with radiation treatment.

Embodiment 82: Use according to embodiment 80 or embodiment 81, wherein the inflammatory skin disease is selected from the group consisting of psoriasis, dermatitis eczema, atopic dermatitis, scleroderma, lichen planus and alopecia areata.

Embodiment 83: A kit of parts comprising a CD4 binding peptide and a psoralen compound together with one or more pharmaceutically acceptable excipients for use as a medicament in the mediation of radiation treatment for treatment of a clinical condition.

Embodiment 84: A kit of parts according to any of embodiments 71 to 83, wherein the psoralen compound is present in a therapeutically effective amount.

Embodiment 85: A kit of parts according to any of embodiments 71 to 84, wherein the CD4 binding peptide is present in a therapeutically effective amount.

Embodiment 86: A kit of parts according to any of embodiments 71 to 85, wherein the CD4 binding peptide is capable of binding to human CD4.

Embodiment 87: A kit of parts according to any of embodiments 71 to 86, wherein the CD4 binding peptide is manufactured using mammalian cell culture.

Embodiment 88: A kit of parts according to any of embodiments 71 to 87, wherein the CD4 binding peptide is capable of activating the p56$^{Ick}$ kinase.

Embodiment 89: A kit of parts according to embodiment 88, wherein activation of p56$^{Ick}$ kinase increases the phosphorylation of at least one of the inhibitory adaptor molecules, Dok-1 and/or SHIP-1.

Embodiment 90: A kit of parts according to any of embodiments 71 to 89, wherein the CD4 binding peptide is an anti-CD4 antibody or a CD4 binding fragment thereof.

Embodiment 91: A kit of parts according to embodiment 90, wherein the antibody is a monoclonal antibody.

Embodiment 92: A kit of parts according to embodiment 90 or embodiment 91, wherein the antibody is a humanized antibody.

Embodiment 93: A kit of parts according to embodiment 90 or embodiment 91, wherein the antibody is a human antibody.

Embodiment 94: A kit of parts according to any of embodiments 90 to 93, wherein the antibody has a light chain of the kappa-type (κ).

Embodiment 95: A kit of parts according to any of embodiments 90 to 94, wherein the antibody is selected from the group consisting of zanolimumab, keliximab, clenoliximab, TNX/355, TRX/1, IOT4a, priliximab, and 4162W94.

Embodiment 96: A kit of parts according to embodiment 95, wherein the antibody is zanolimumab.

Embodiment 97: A kit of parts according to any of embodiments 71 to 96, wherein the psoralen compound is of the general formula:

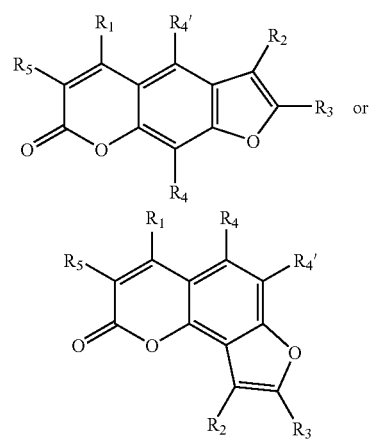

wherein $R_1$, $R_2$, $R_3$, $R_4$, $R_4'$ and $R_5$ individually are selected from the group consisting of hydrogen, halogen, $C_{(1-10)}$-alkyl, and $C_{(1-10)}$-alkyl substituted with halogen, amine or hydroxyl, and $C_{(1-10)}$-ethers optionally substituted with hydroxy; or $R_1$ and $R_5$ together form a pyrido.

Embodiment 98: A kit of parts according to any of embodiments 71 to 97, wherein the psoralen compound is selected from the group consisting of pyrido-[3,4-c]psoralen, 7-methylpyrido-[3,4-c]psoralen, 5-methoxypsoralen, 8-methoxypsoralen, 4,5',8-trimethylpsoralen, 4-methylpsoralen, 4,4-dimethylpsoralen, 4-5'-dimethylpsoralen, 4',8-methoxypsoralen, 4'-(omega-amino-2-oxa)alkyl-4,5',8-trimethylpsoralen, 4'-(4-amino-2-oxa)-butyl-4,5',8-trimethylpsoralen, 4'-chloromethyl-4,5',8-trimethylpsoralen, 4'-aminomethyl-4,5',8-trimethylpsoralen, 4'-(2-hydroxyethoxy)-methyl-4,5',8-trimethylpsoralen, 4'-(6-hydroxyhexyloxy)-methyl-4,5',8-trimethylpsoralen, 4'-hydroxymethyl-4,5',8-trimethylpsoralen, 5-methyl-angelicin and 2H-furo[2,3-h][1]benzopyran-2-one.

Embodiment 99: A kit of parts according to embodiment 98, wherein the psoralen compound is 5-methoxypsoralen or 8-methoxypsoralen.

Embodiment 100: A kit of parts according to any of embodiments 71 to 99, wherein the kit of parts is formulated in a unit dosage form, wherein each unit dosage of CD4 binding peptide comprises peptide in the range of 20 mg to 2000 mg.

Embodiment 101: The kit of parts according to any of embodiments 71 to 100, wherein the kit of parts is formulated in a unit dosage form, wherein each unit dosage of psoralen comprises the psoralen compound in the range of 10 to 50 mg.

Embodiment 102: A kit of parts according any of embodiments 71 to 101, wherein the CD4 binding peptide is in a formulation suitable for parenteral administration.

Embodiment 103: A kit of parts according to any of embodiments 71 to 102, wherein the CD4 binding peptide is formulated as a solution or a powder suitable for preparation of a suspension or a solution.

Embodiment 104: A kit of parts according to any of embodiments 71 to 103, wherein the psoralen compound is in a formulation suitable for oral or topical administration.

Embodiment 105: The kit according to any of embodiments 71 to 104, wherein the psoralen compound is formulated in a form selected from the group consisting of tablets, capsules, crèmes, lotions or ointments.

Embodiment 106: A CD4 binding peptide for use in the treatment of a malignant disease or an inflammatory skin disease in an individual who receives or will receive radiation treatment.

Embodiment 107: A CD4 binding peptide for use in the treatment of a malignant disease or an inflammatory skin disease in combination with radiation treatment.

Embodiment 108: A CD4 binding peptide for use in the mediation of radiation treatment of a clinical condition.

Embodiment 109: A CD4 binding peptide according to any of embodiments 106 to 108, wherein the CD4 binding peptide is capable of binding to human CD4.

Embodiment 110: A CD4 binding peptide according to any of embodiments 106 to 109, wherein the CD4 binding peptide is manufactured using mammalian cell culture.

Embodiment 111: A CD4 binding peptide according to any of embodiments 106 to 110, wherein the CD4 binding peptide is capable of activating the $p56^{lck}$ kinase.

Embodiment 112: A CD4 binding peptide according to embodiment 111, wherein the activation of $p56^{lck}$ kinase increases the phosphorylation of at least one of the inhibitory adaptor molecules, Dok-1 and/or SHIP-1.

Embodiment 113: A CD4 binding peptide according to any of embodiments 106 to 112, wherein the CD4 binding peptide is an anti-CD4 antibody or a CD4 binding fragment thereof.

Embodiment 114: A CD4 binding peptide according to embodiment 113, wherein the antibody is a monoclonal antibody.

Embodiment 115: The use according to embodiment 113 or embodiment 114, wherein the antibody is a humanized antibody.

Embodiment 116: A CD4 binding peptide according to embodiment 113 or embodiment 114, wherein the antibody is a human antibody.

Embodiment 117: A CD4 binding peptide according to any of embodiments 113 to 116, wherein the antibody has a light chain of the kappa-type (K).

Embodiment 118: A CD4 binding peptide according to any of embodiments 113 to 117, wherein the antibody is selected from the group consisting of zanolimumab, keliximab, clenoliximab, TNX/355, TRX/1, IOT4a, priliximab, and 4162W94.

Embodiment 119: A CD4 binding peptide according to embodiment 118, wherein the antibody is zanolimumab.

Embodiment 120: A CD4 binding peptide according to any of embodiments 106 to 119, wherein the radiation treatment is selected from the group consisting of a combination of administration of a psoralen compound and long-wave ultraviolet radiation (PUVA); UVB; narrow band UVB; high dose UVA; electron beam; and x-ray.

Embodiment 121: A CD4 binding peptide according to embodiment 120, wherein the radiation treatment is a combination of administration of a psoralen compound and long-wave ultraviolet radiation (PUVA).

Embodiment 122: A CD4 binding peptide according to embodiment 121 wherein the psoralen compound has a general formula:

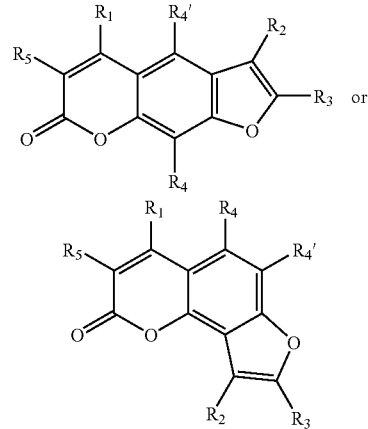

wherein $R_1$, $R_2$, $R_3$, $R_4$, $R_4'$ and $R_5$ individually are selected from the group consisting of hydrogen, halogen, $C_{(1-10)}$-alkyl, and $C_{(1-10)}$-alkyl substituted with halogen, amine or hydroxyl, and $C_{(1-10)}$-ethers optionally substituted with hydroxy; or $R_1$ and $R_5$ together form a pyrido.

Embodiment 123: A CD4 binding peptide according to any of embodiments 106 to 122, wherein the psoralen compound is selected from the group consisting of pyrido-[3,4-c]psoralen, 7-methylpyrido-[3,4-c]psoralen, 5-methoxypsoralen, 8-methoxypsoralen, 4,5',8-trimethylpsoralen, 4-methylpsoralen, 4,4-dimethylpsoralen, 4-5'-dimethylpsoralen, 4',8-methoxypsoralen, 4'-(omega-amino-2-oxa)alkyl-4,5',8-trimethylpsoralen, 4'-(4-amino-2-oxa)-butyl-4,5',8-trimethylpsoralen, 4'-chloromethyl-4,5',8-trimethylpsoralen, 4'-aminomethyl-4,5',8-trimethylpsoralen, 4'-(2-hydroxyethoxy)-methyl-4,5',8-trimethylpsoralen, 4'-(6-hydroxyhexyloxy)-methyl-4,5',8-trimethylpsoralen, 4'-hydroxymethyl-4,5',8-trimethylpsoralen, 5-methyl-angelicin and 2H-furo[2,3-h][1]benzopyran-2-one.

Embodiment 124: A CD4 binding peptide according to embodiment 123, wherein the psoralen compound is 5-methoxypsoralen or 8-methoxypsoralen.

The methods of treatment described herein may also be combined with other treatments, in particular with other treatments conventionally used for the treatment of the particular clinical condition. For example, in embodiments of the invention wherein the clinical condition is a malignant disease the treatment may be combined with a chemotherapy, treatment by surgery, treatment with immunostimulating substances, gene therapy, treatment with other peptides, such as antibodies and/or treatment using dendritic cells.

EXAMPLES

Example 1

Inhibition of T-cell Signaling in Activated T Cells by Zanolimumab.

This example demonstrates the inhibitory actions of zanolimumab (GenMab, Denmark) on activation of T cells via the T-cell receptor (TCR). The results are shown in FIG. 2.

The effect on T-cell signaling molecules upon T-cell activation presented in FIG. 2 were obtained with CD4$^+$ T cells isolated from peripheral blood from healthy donors. CD4$^+$ T cells were isolated using enrichment RosetteSep cocktail (Stemcell Technologies Inc, Canada) and separated by lymphoprep (Axis Shield, Poc AS, Norway) density centrifugation. CD4$^+$ T cells ($10^7$ cells) were incubated with zanolimumab and then stimulated with CD3 monoclonal antibody (OKT3, available from Orthoclone, Pharmacy, UMC, Utrecht) immobilized onto latex beads. Cell were lysed using lysis buffer (1% Nonidet P-40, 20 mM Tris-HCl, pH 7.4, 150 mM NaCl, 2 mM EGTA, 1 mM Na$_3$VO$_4$, 10 mM NaF, 10 mM sodium pyrophosphate and protease inhibitors (Roche Molecular Biochemicals, Sussex, UK)). Proteins in duplicate cell lysate samples were separated by 7-15% gradient gel SDS-PAGE and transferred onto blotting membranes by electrophoresis. Membranes were incubated with antibodies for specific tyrosine-phosphorylated proteins, stripped and then re-probed with antibodies recognizing the specific proteins regardless of their phosphorylation status. Proteins were detected with an HRP-conjugated secondary antibody, visualized by ECL and quantified using a phosphor-imager.

The results in FIG. 2 demonstrate that zanolimumab causes a generalized inhibition of tyrosine-phosphorylation of intracellular proteins following TCR stimulation via immobilized CD3 monoclonal antibody (FIG. 2A). Proteins of 21 kDa and 23 kDa are markedly inhibited in their phosphorylation and are identified as the p21 and p23 phosphorylated isomers of the TCR-ζ chain (FIG. 2A). The observed inhibition of the phosphorylation of the downstream tyrosine kinase 'zeta-chain-associated protein 70' (ZAP-70) by zanolimumab is in line with this (FIG. 2B). Previously, the activation of TCRζ and subsequently of ZAP-70 was shown to be induced by the tyrosine kinase p56$^{lck}$ (Chan A C et al., Annu Rev Immunol. 12, 555-92 (1994), van Oers N S et al., J Exp Med. 183(3), 1053-1062 (1996), Weiss A et al., 76(2), 263-74 (1994), which is associated to the cytoplasmic tail of CD4 (Rudd C E, Proc Natl Acad Sci USA. 85(14), 5190-5194 (1988), Veillette 1988 supra). The prominent tyrosine-phosphorylated protein of 36-38 kDa, of which the phosphorylation is also inhibited by zanolimumab, is identified as the 'adaptor protein linker for activation of T cell' (LAT) (FIG. 2A). In addition, zanolimumab inhibits three downstream signaling pathways that play a critical role in T-cell activation: Erk1/2, p38 serine/threonine and AKT/PKB (FIG. 2C).

In summary, zanolimumab inhibits the very earliest T-cell activation events by about 50%, which is likely p56$^{lck}$-dependent, and a comparable level of inhibitory action is thereby transmitted to multiple downstream signaling pathways.

Example 2

Direct Inhibitory Signaling in T Cells by Zanolimumab.

This example demonstrates the direct inhibitory signaling by zanolimumab in T cells. The results are shown in FIG. 3.

The activation of inhibitory adaptor molecules in T cells presented in FIG. 3 were obtained with CD4$^+$ T cells isolated as described in example 1. CD4$^+$ T cells (3×10E7 cells) were incubated with zanolimumab and, when appropriate, pre-incubated with Src kinase inhibitors PP2 or damnacanthal (Merck Biosciences, Nottingham, UK) before exposure to zanolimumab. Cell lysates were incubated with CD4-precipitating antibody and antibody-bound proteins were precipitated with protein-G sepharose. For precipitation of SH2-binding proteins, lysates were incubated with SH2C-RasGAP-GST coupled to glutathione agarose beads. CD4-precipitates were incubated in kinase buffer (40 mM HEPES pH 7.4, 10 mM MgCl$_2$, 3 mM MnCl$_2$, 200 μM Na$_3$VO$_4$ in 10% glycerol) containing 1 mM DTT, 5 μM ATP and 1 μCi $^{32}$Pγ-ATP. The reaction was stopped by boiling in Laemmli's buffer. Proteins were separated by 7-15% gradient gel SDS-PAGE and transferred onto blotting membranes by electrophoresis. Dried membranes were exposed to radiography-sensitive film and then incubated with antibodies for specific proteins. Proteins were detected with an HRP-conjugated secondary antibody, visualized by ECL and quantified using a phosphor-imager.

The results in FIG. 3 show that zanolimumab causes optimal stimulation of CD4-associated p56$^{lck}$ tyrosine kinase activity, phosphorylation of α-casein as an exogenous p56$^{lck}$ substrate and p56$^{lck}$ autophosphorylation (FIG. 3A). The increased activity of p56$^{lck}$ induced by zanolimumab may seem to conflict with data showing the impaired T-cell activation upon zanolimumab incubation (FIG. 2). One possible explanation is outlined below, however the present invention is not bound by a specific underlying mechanism. We hypothesize that zanolimumab may cause sequestration of p56$^{lck}$ away from the TCR. In addition, zanolimumab may directly generate a negative signal through p56$^{lck}$, as p56$^{lck}$ has been shown to play a role in the phosphorylation and thereby activation of the inhibitory adaptor proteins 'downstream of tyrosine kinase' (Dok-1) (Martelli 2001 supra, Okabe 2005 supra) and 'SH2 domain contacting 5'-inositol phasphatase' (SHIP-1) (Lamkin 1997 supra). Zanolimumab indeed induces phosphorylation of Dok-1 and SHIP-1 (FIG. 3B, 3C). The direct link between the observed increase in p56$^{lck}$ activation by zanolimumab and induction of Dok-1 activation is confirmed via pre-treatment of the cells with the Src inhibitor PP2 or with the more specific p56$^{lck}$ inhibitor damnacanthal. Pre-treatment with these inhibitors leads to a reduced amount of precipitated Dok-1 (FIG. 3D). In summary, CD4 binding by zanolimumab causes p56$^{lck}$ kinase activation, which in turn leads to increased Dok-1 and SHIP-1 phosphorylation.

Example 3

Influence of Zanolimumab in Combination with UV Treatment on Primary CD4$^+$ T Cells.

Total CD4$^+$ T cells, or CD45RO$^+$ and CD45RA$^+$ subsets, are isolated from blood bank leukopheresis packs obtained from healthy donors of both sexes. Sterile PBS is added to each blood pack, and peripheral blood mononuclear cells (PBMC) separated by lymphoprep density centrifugation (Lymphocyte Separation Medium; BioWhittaker, via Cambrex Verviers, Belgium; product# 17-829E) at 800×g for 20 min (brake 0) for 20 minutes. PBMC at the gradient interface are removed and washed 3 times in PBS (400×g for 7 min, brake 3) before re-suspension in RPMI. CD4$^+$ T cells are isolated by negative selection using Dynal® CD4$^+$ T-Cell Negative Isolation Kit (Dynal Biotech GmbH, Hamburg, Germany; product# 113.11) according to the manufacturer's protocol. The CD4$^+$ CD45RA$^+$ and CD4$^+$ CD45R0$^+$ T cell subsets are isolated from the PBMC suspension with the Dynal® CD4$^+$ T-Cell Negative Isolation Kit (Dynal Biotech GmbH, Hamburg, Germany; product# 113.17) in combination with mouse monoclonal antibody against CD45R0+ (Becton Dickinson, cat no 555491)) and CD45RA+ (Becton Dickinson, cat no 556625) cells in combination with anti-mouse magnetic beads. The percentage of CD4$^+$ T-cells is checked by flow cytometry via staining with zanolimumab-FITC (Genmab B.V.; batch# 200302), and anti-CD3-PE (Becton Dickinson, cat no 556612), and in case of CD4$^+$ CD45RA$^+$ and CD4$^+$ CD45R0+ T cell subsets with anti-CD45RA-FITC and CD45RO-PE antibodies, and analysis of cell-associated fluorescence on a FACS Calibur using Cell Quest software (Becton Dickinson, Erembodegem-Aalst, Belgium).

After acclimatization of the isolated CD4+ T cells, and CD4+ CD45RA+ and CD4+CD45R0+ T cell subsets cells for 1 hours in culture medium (RPMI 1640 supplemented with 10% heat-inactivated fetal calf serum (Fetal clone II-Hyclone; product# SH30066.3), 2 mM L-glutamine (BioWhittaker, via Cambrex; product# 17-605F) and 50 units/ml penicillin and 50 µg/ml streptomycin (BioWhittaker, via Cambrex; product# DE17-603E)), the cells are re-suspended in culture medium alone, in culture medium with 10 µg/ml zanolimumab (Genmab, Denmark), and in culture medium containing 10 µg/ml HuMab-KLH (Genmab B.V.; control IgGκ). These batches are treated with various doses of UV (50-1000 J/m$^2$) with a UV cross linker (UV Stratalinker 2400, Stratagene) and the amount of cell going into apoptosis is established at 0, 4, 8, 24, and 48 hours by three separate assays. First, for the Annexin-V staining method, analysis is done using Annexin-V-FITC and 7-AAD (7-aminoactinomycin D) (BD Biosciences) by flow cytometry, and Annexin-V-FITC+/7-AAD+ cells are counted as apoptotic. Second, for the intracellular Caspase-3 staining method, CD4+ T cells will be washed twice in FACS buffer (PBS with 2% HIFCS and 0.01% azide) before re-suspension in Cytofix/Cytoperm (BD Biosciences). Following incubation at 4° C. for 20 min, cells are washed twice in permeabilization/wash buffer (BD Biosciences) before staining with active caspase-3 monoclonal antibody (BD Biosciences) followed by flow cytometry, and caspase-3 positive cells are counted as apoptotic. For analysis with 3,3'-dihexyloxacarbocyanine iodide (DiOC$_6$) (Aldrich, Poole, Dorset, UK) method, cells are stained with 23 ng/ml DiOC$_6$ prior to flow cytometry. Cells exhibiting a loss of FSC and DiOC$_6$ intensity are counted as apoptotic.

Example 4

Influence of Zanolimumab in Combination with UV Treatment on CD4+ T Cell Lines.

The CD4+ T cell lines SUP-T1 (ATCC, order nr CRL-1942), CEM-NKr (NIH AIDS Research and Reference Reagent Program; reagent nr 458) are cultured in culture medium (RPMI 1640 supplemented with 10% heat-inactivated fetal calf serum (Fetal clone II-Hyclone; product# SH30066.3), 2 mM L-glutamine (BioWhittaker, via Cambrex; product# 17-605F) and 50 units/ml penicillin and 50 µg/ml streptomycin (BioWhittaker, via Cambrex; product# DE17-603E)) in 5% CO$_2$-95% air at 37° C., at optimal cell densities of 3-10×10$^5$ cells/ml.

The cells are re-suspended in culture medium alone, in culture medium with 10 µg/ml zanolimumab (Genmab, Denmark), and in culture medium containing 10 µg/ml HuMab-KLH (Genmab B.V.; control IgG1,k). These batches are treated with various doses of UV (50-1000 J/m$^2$) with a UV cross linker (UV Stratalinker 2400, Stratagene) and the amount of cells going into apoptosis is established at 0, 4, 8, 24, and 48 hours by three separate assays. First, for the Annexin-V staining method analysis are done using Annexin-V-FITC and 7-MD (7-aminoactinomycin D) (BD Biosciences) by flow cytometry, and Annexin-V-FITC+/7-AAD+ cells are counted as apoptotic. Second, for the intracellular Caspase-3 staining method, CD4+ T cells are washed twice in FACS buffer (PBS with 2% HIFCS and 0.01% azide) before re-suspension in Cytofix/Cytoperm (BD Biosciences). Following incubation at 4° C. for 20 min, cells are washed twice in permeabilisation/wash buffer (BD Biosciences) before staining with active caspase-3 monoclonal antibody (BD Biosciences) followed by flow cytometry, and caspase-3 positive cells are counted as apoptotic. For analysis with 3,3'-dihexyloxacarbocyanine iodide (DiOC$_6$) (Aldrich, Poole, Dorset, UK) method, cells are stained with 23 ng/ml DiOC$_6$ prior to flow cytometry. Cells exhibiting a loss of FSC and DiOC$_6$ intensity are counted as apoptotic.

Example 5

Influence of Zanolimumab in Combination with PUVA Treatment on Primary CD4+ T Cells.

Primary CD4+ T cells, and CD4+ CD45RA+ and CD4+ CD45R0+ T cell subsets cells, are isolated as described in Example 3.

After acclimatization of the isolated cells for a minimal of 1 hours in culture medium (RPMI 1640 supplemented with 10% heat-inactivated fetal calf serum (Fetal clone II-Hyclone; product# SH30066.3), 2 mM L-glutamine (BioWhittaker, via Cambrex; product# 17-605F) and 50 units/ml penicillin and 50 µg/ml streptomycin (BioWhittaker, via Cambrex; product# DE17-603E)), the cells are re-suspended in culture medium alone, in culture medium with 10 µg/ml zanolimumab (Genmab), and in culture medium containing 10 µg/ml HuMab-KLH (Genmab B.V.; control IgG1,k). These cells are cultured for 0, 0.3, 1, 2, 4, and 8 hours in 5% CO$_2$-95% air at 37° C. After culturing, cells are washed in serum free medium. Cells are split into two portions: one portion is incubated with 8-MOP (8-methoxypsoralen 200 ng/ml) in serum free medium for 5 min at RT, and the other portion is incubated in serum free medium alone for 5 min at RT. Then, cells are exposed to various doses of UV (50-1000 J/m$^2$) with a UV cross linker (UV Stratalinker 2400, Stratagene). After treatment the cells are incubated in culture medium, and the amount of cell going into apoptosis is established at 0, 4, 8, 12, 24, and 48 hours by three separate assays. First, for the Annexin-V staining method analysis is done using Annexin-V-FITC and 7-AAD (7-aminoactinomycin D) (BD Biosciences) by flow cytometry, and Annexin-V-FITC+/7-AAD+ cells are counted as apoptotic. Second, for the intracellular Caspase-3 staining method, CD4+ T cells will be washed twice in FACS buffer (PBS with 2% HIFCS and 0.01% azide) before re-suspension in Cytofix/Cytoperm (BD Biosciences). Following incubation at 4° C. for 20 min, cells are washed twice in permeabilisation/wash buffer (BD Biosciences) before staining with active caspase-3 monoclonal antibody (BD Biosciences) followed by flow cytometry, and caspase-3 positive cells are counted as apoptotic. For analysis with 3,3'-Dihexyloxacarbocyanine iodide (DiOC$_6$) (Aldrich, Poole, Dorset, UK) method, cells are stained with 23 ng/ml DiOC$_6$ prior to flow cytometry. Cells exhibiting a loss of FSC and DiOC$_6$ intensity are counted as apoptotic.

Example 6

Influence of Zanolimumab in Combination with PUVA Treatment on CD4+ T Cell Lines.

The cell lines SUP-T1 and CEM-NKr are described in Example 4. The cells are re-suspended in culture medium alone, in culture medium with 10 µg/ml zanolimumab (Genmab), and in culture medium containing 10 µg/ml HuMab-KLH (Genmab B.V.; control IgG1,k). These cells are cultured for 0, 0.3, 1, 2, 4, and 8 hours in 5% CO$_2$-95% air at 37° C. After culturing, cells are washed in serum free medium. Cells are split into two portion: one portion is incubated with 8-MOP (Methoxsalen 200 ng/ml) in serum free medium for 5 min at RT, and the other portion is incubated in serum free medium alone for 5 min at RT. Then, cells are exposed to various doses of UV (50-1000 J/m$^2$) with a UV cross linker (UV Stratalinker 2400, Stratagene). After treatment the cells are incubated in culture medium, and the amount of cell going into apoptosis is established at 0, 4, 8, 12, 24, and 48 hours by three separate assays. First, for the Annexin-V staining method analysis is done using Annexin-V-FITC and 7-AAD (7-aminoactinomycin D) (BD Biosciences) by flow cytometry, and Annexin-V-FITC+/7-AAD+ cells are counted as apoptotic. Second, for the intracellular Caspase-3 staining method, CD4$^+$ T cells will be washed twice in FACS buffer (PBS with 2% HIFCS and 0.01% azide) before re-suspension in Cytofix/Cytoperm (BD Biosciences). Following incubation at 4° C. for 20 min, cells are washed twice in permeabilisation/wash buffer (BD Biosciences) before staining with active caspase-3 monoclonal antibody (BD Biosciences) followed by flow cytometry, and caspase-3 positive cells are counted as apoptotic. For analysis with 3,3'-Dihexyloxacarbocyanine iodide (DiOC$_6$) (Aldrich, Poole, Dorset, UK) method, cells are stained with 23 ng/ml DiOC$_6$ prior to flow cytometry. Cells exhibiting a loss of FSC and DiOC$_6$ intensity are counted as apoptotic.

Example 7

(P)UVA-induced Apoptosis of G1 Phase T Cells.

SUP-T1 and CEM-NKr cell lines will be synchronized with 0.5-50 μg/ml aphidicolin for 5-18 hr, and cells will accumulate in the G1/S boundary. Cell cycle arrest will be released by washing the cells with PBS three times, and returning these to normal culture medium, and cultivated for 4-6 h. After that, nocodazole (200 μg/ml) will be added to the culture medium and will be cultured for further 6 h. By this procedure, almost all cells will synchronize in the M phase. By washing out the nocodazole three times with PBS, and re-suspending in normal medium, the synchronized cells will move to the G1 phase within 1 h. At 10, 20, 30, 40, 50, and 60 min cells will be treated with various doses of UV (50-1000 J/m$^2$) with a UV cross linker (UV Stratalinker 2400, Stratagene) and the amount of cell going into apoptosis will be established by three separate assays. First, for the Annexin-V staining method analysis will be done using Annexin-V-FITC and 7-AAD (7-aminoactinomycin D) (BD Biosciences) by flow cytometry, and Annexin-V-FITC+/7-AAD+ cells will be counted as apoptotic. Second, for the intracellular Caspase-3 staining method, CD4$^+$ T cells will be washed twice in FACS buffer (PBS with 2% HIFCS and 0.01% azide) before re-suspension in Cytofix/Cytoperm (BD Biosciences). Following incubation at 4° C. for 20 min, cells will be washed twice in permeabilisation/wash buffer (BD Biosciences) before staining with active caspase-3 monoclonal antibody (BD Biosciences) followed by flow cytometry, and caspase-3 positive cells will be counted as apoptotic. For analysis with 3,3'-Dihexyloxacarbocyanine iodide (DiOC$_6$) (Aldrich, Poole, Dorset, UK) method, cells will be stained with 23 ng/ml DiOC$_6$ prior to flow cytometry. Cells exhibiting a loss of FSC and DiOC$_6$ intensity will be counted as apoptotic.

Example 8

(P)UVA Treatment Followed by NK Cell Mediated ADCC of Primary CD4+ T Cells, Induction of Cell Lysis Peripheral human blood from healthy volunteers (after informed consent) is collected by vena puncture and provide in the form of a buffy coat (Sanquin, Utrecht, The Netherlands). Sterile PBS is added to the human blood, and peripheral blood mononuclear cells (PBMC) are separated by lymphoprep density centrifugation (Lymphocyte Separation Medium; BioWhittaker, via Cambrex Verviers, Belgium; product# 17-829E) at 800×g (brake 0) for 20 minutes (Heraeus Multifuge 3S-R). PBMC are removed from the gradient interface and washed 3 times in PBS (400×g for 7 min, brake 3) before resuspending in PBS supplemented with 0.1% BSA.

CD4+ T cells (or CD45RO+ and CD45RA+ subsets) are isolated by negative selection using Dynal® CD4 Negative Isolation Kit (Dynal Biotech GmbH, Hamburg, Germany; product# 113.17) according to the manufacturer's protocol.

The CD4+ CD45RA+ or CD4+ CD45RO+ T cell subset are isolated from the PBMC suspension using the Dynal® CD4 Negative Isolation Kit in combination with mouse mAb against CD45R0+ (Becton Dickinson, cat# 555491), or CD45RA+ (Becton Dickinson, cat# 556625) cells in combination with anti-mouse magnetic beads. The percentage of CD4+ T-cells is checked by flow cytometry via staining with HuMax-CD4-FITC (Genmab B.V.; batch# 200302), and anti-CD3-PE (Becton Dickinson, cat no 556612), and in case of CD4+ CD45RA+ and CD4+ CD45R0+ T cell subsets with anti-CD45RA-FITC and CD45RO-PE antibodies respectively. Cell-associated fluorescence is analyzed on a FACS Calibur using Cell Quest software (Becton Dickinson, Erembodegem-Aalst, Belgium).

NK-cells are isolated from peripheral human blood by negative selection using Dynal® NK Cell Negative Isolation Kit (Dynal Biotech GmbH, Hamburg, Germany; product# 113.15) according to the manufacturer's protocol. The percentage of NK cells is checked by flow cytometry via staining with CD56-PE (Becton Dickinson, cat# 555516) and CD16-FITC (Becton Dickinson, cat# 555406), and cell-associated fluorescence is analyzed on a FACS Calibur using Cell Quest software (Becton Dickinson, Erembodegem-Aalst, Belgium).

Isolated NK cells are cultured at 37° C., 5% $CO_2$ in RPMI 1640 (Cambrex, cat# BE12-115F) supplemented with 10% heat-inactivated Cosmic Calf Serum (CCS), 50 μg/ml Streptomycin and 50 U/ml Penicillin (Cambrex, cat# DE17-603E), 2 mM L-Glutamine (Cambrex, cat# BE17-605F) and 200-300 U/ml IL-2 until CD4+ T-cells are PUVA treated (after 2 days).

The isolated CD4$^+$ T-cells, or isolated CD4+ CD45RA+ and CD4+ CD45RO+ subsets, are labelled with the fluorescent cell membrane label PKH26 (FL2) (PKH26 Red Fluorescent Cell Linker Kit, Sigma-Aldrich Chemie, Zwijndrecht, The Netherlands; product# PKH26-GL) according to manufacturer's protocol.

PKH26-labeled CD4+ T-cells (or isolated subsets) are transferred to 96-well flat-bottom plates (coated with 10 μg/ml OKT3 (Orthoclone, cat# 01KS34H) at 1*10$^5$ cells/well in 100 μl.

Next, 50 μl CD28 (CLB, cat# M1650; final concentration is 2 μg/ml) is added. Finally, 50 μl diluted zanolimumab is added to give a final volume of 200 μl/well.

These CD4+ T-cells are incubated at 37° C., 5% $CO_2$ for 2 days. After culturing, cells are split into two equal portions: one portion is incubated with 1 μg/ml 8-MOP (Psoralen; Fluka, cat# 95560) for 30 min at RT, and the other portion is incubated without 8-MOP for 30 min at RT.

Next, cells are irradiated with 1 J/cm2 UVA at various distances from UVA lamp (UVP® 8W model UVLMS-38) for different time periods.

The cultured NK-cells are washed 3 times in PBS (400×g for 7 min, brake 3) before resuspending in culture medium at 2.5-5*10$^6$ cells/ml (depending on the NK-cell yield after culturing and washing).

After irradiation, the PKH26-labeled and (P)UVA treated CD4+ T-cells are transferred to 96 well round-bottom plates at 2.5-5*10$^4$ cells/well in 100 μl (depending on the NK-cell yield after culturing and washing in culture medium).

Subsequently, 100 µl NK cells are added at 2.5-5*10⁵ cells/well (the amount of NK cells per well is adjusted to obtain a 10:1 effector:target cell ratio), and cells are spun down (54×g for 10 seconds, brake 3). The pelleted cells are incubated for 0, 4 and 24 hours in 5% $CO_2$ at 37° C. For measurement of spontaneous lysis, target cells are incubated with culture medium in the absence of NK cells.

After incubation, cells are spun down (500×g for 5 min, brake 3) and transferred cells to Micronic FACS tubes with 100 ul FACS buffer. Cells are stained with TO-PRO®-3 (Molecular Probes, Leiden, The Netherlands; product# T3605; 1:100,000 final dilution) just before analysis. TO-PRO-3 iodide is a fluorescent stain for nucleic acids after entering through the permeable membrane of a lysed T cell and is measurable in FL4. Cell-associated fluorescence is assessed by flow cytometry using a FACSCalibur™ and Cell Quest Pro software (Becton Dickinson) with appropriate compensation settings. The percentage cell lysis is calculated by dividing the number of TO-PRO®-3+ cells within the PKH26+ cell population by the total number of PKH26+ cells.

Example 9

Application in a Clinical Setting

In one embodiment of the invention, a patient suffering from a malignant disease or an inflammatory skin disease, is exposed to PUVA prior to administration of a CD4 binding peptide, e.g. the patient may be exposed to PUVA treatment according to the description for one week, two weeks or two to four weeks before administration of a CD4 binding peptide is initiated. The administration of CD4 binding peptide may be continued either alone or during continued treatment with PUVA. In one embodiment, the PUVA treatment and the administration of CD4 binding peptide is initiated and performed simultaneously. In one embodiment the CD4 binding peptide is Zanolimumab (Genmab, Denmark). In one embodiment, the CD4 binding peptide is administered in a dosage of 700 mg by intravenous infusion over 2-3 hours. The initial dosage is followed by maintenance dosages of 350 mg of CD4 binding peptide every 2 weeks as necessary until a significant improvement in clinical symptoms appear, or until the symptoms disappear. In one embodiment, the dosage of CD4 binding peptide is increased gradually, until effect on symptoms is observed, or until unacceptable side effects occur. The treatment regimen is repeated one or more time every 3-9 months as necessary. The patients may simultaneously be treated with other established treatment regimens.

In one embodiment, a psoralen is applied to the patient before initiation of PUVA and CD4 binding peptide treatment. In one embodiment, a psoralen is applied simultaneously or after initiation of PUVA and CD4 binding peptide treatment.

The invention claimed is:

1. A method of treatment of a CD4+ T-cell lymphoma comprising administering to a subject in need thereof a therapeutically effective amount of an antibody, or antigen-binding fragment thereof, comprising heavy and light chain variable region sequences as set forth in SEQ ID NOs: 1 and 2, respectively, and radiation treatment, wherein the radiation treatment is selected from the group consisting of psoralen and long-wave ultraviolet radiation (PUVA): UVB; narrow band UVB; high dose UVA; electron beam; x-ray; and photopheresis, wherein the psoralen is a photosensitizer.

2. A method according to claim 1, wherein the CD4+ T-cell lymphoma is a CD4+ cutaneous T-cell lymphoma.

3. A method according to claim 1, wherein the CD4+ T-cell lymphoma is a CD4+nodal T-cell lymphoma.

4. A method according to claim 1, wherein the CD4+ lymphoma is selected from the group consisting of peripheral T-cell lymphoma, angioimmunoblastic T-cell lymphoma and anaplastic large T-cell lymphoma.

5. A method according to claim 1, wherein the CD4+ T-cell lymphoma is refractory to at least one other treatment modality.

6. A method according to claim 1, wherein the antibody, or antigen-binding fragment thereof, is manufactured using mammalian cell culture.

7. A method according to claim 1, wherein the antibody, or antigen-binding fragment thereof, activates p56 kinase.

8. A method according to claim 7, wherein the activation of p56 kinase increases the phosphorylation of Dok-1 and/or SHIP-I.

9. A method according to claim 1, wherein the antibody, or antigen-binding fragment thereof, upon binding to a CD4+ cell, activates natural killer cells.

10. A method according to claim 1, wherein the antibody is a monoclonal antibody.

11. A method according to claim 1, wherein the antibody is a human antibody.

12. A method according to claim 1, wherein the antibody has a light chain of the kappa-type (K).

13. A method according to claim 1, wherein the antibody is zanolimumab.

14. A method according to claim 1, wherein the radiation treatment is PUVA.

15. A method according to claim 14, wherein a psoralen compound is administered prior to UVA treatment.

16. A method according to claim 15, wherein the psoralen compound has a general formula:

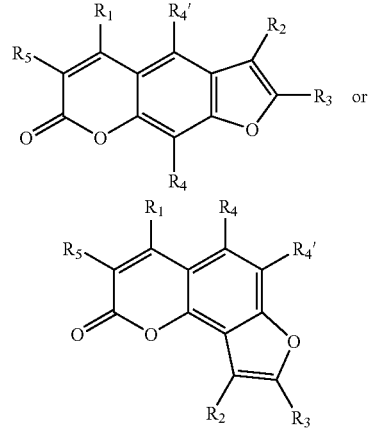

wherein $R_1$, $R_2$, $R_3$, $R_4'$ and $R_5$ individually are selected from the group consisting of hydrogen, halogen, $C_{(1-10)}$-alkyl, $C_{(1-10)}$-alkyl substituted with halogen, amine or hydroxyl, and $C_{(1-10)}$-ethers optionally substituted with hydroxy; or $R_1$ and $R_5$ together form a pyrido, and wherein $R_4$ is individually selected from the group consisting of hydrogen, halogen, $C_{(1-10)}$-alkyl, and $C_{(1-10)}$-alkyl substituted with halogen or amine, and $C_{(1-10)}$-ethers optionally substituted with hydroxy.

17. A method according to claim 16, wherein the psoralen compound is selected from the group consisting of pyrido-[3,4-c]psoralen, 7-methylpyrido-[3,4-c]psoralen, 5-methoxypsoralen, 8-methoxypsoralen, 4,5', 8-trimethylpsoralen, 4-methylpsoralen, 4,4-dimethylpsoralen, 4-5'-dimethylpsoralen, 4',8-methoxy-psoralen, 4'-(omega-amino-2-oxa)alkyl-4,5',8-trimethylpsoralen, 4'-(4-amino-2-oxa)-butyl-4,5',8-trimethylpsoralen, 4'-chloromethyl-4,5',8-trimethylpsoralen, 4'-amino-methyl-4,5', 8-trimethylpsoralen, 4'-(2-hydroxyethoxy)-methyl-4,5', 8-trimethyl-psoralen, 4'-(6-hydroxyhexyloxy)-methyl-4,5', 8-trimethylpsoralen, 4'-hydroxymethyl-4,5',8-trimethylpsoralen, 5-methyl-angelicin and 2H-furo[2,3-h][1]benzopyran-2-one.

18. A method according to claim 17, wherein the psoralen compound is 5-methoxypsoralen or 8-methoxypsoralen.

19. A method according to claim 15, wherein the psoralen compound is administered in a period of from 5 to 0.5 hours before the radiation treatment.

20. A method according to claim 19, wherein the psoralen compound is administered in a period of from 2 to 1 hours before the radiation treatment.

21. A method according to claim 1, wherein the antibody, or antigen-binding fragment thereof, is administered by intravenous, subcutaneous or intramuscular injection.

22. A method according to claim 1, wherein the antibody, or antigen-binding fragment thereof, is administered at least once before the radiation treatment.

23. A method according to claim 1, wherein the antibody, or antigen-binding fragment thereof, is administered once a week.

24. A method according to claim 1, wherein the subject is administered radiation treatment in the range of 1 to 5 times weekly.

25. A method according to claim 1, wherein the antibody, or antigen-binding fragment thereof, and at least one radiation treatment is administered within the same week.

26. A method according to claim 1, wherein the antibody, or antigen-binding fragment thereof, and the radiation treatment are administered within a period of from 4 to 30 weeks.

27. A method according to claim 26, wherein the antibody, or antigen-binding fragment thereof, and the radiation treatment are administered within a period of from 8 to 16 weeks.

28. A method according to claim 27, wherein the antibody, or antigen-binding fragment thereof, and the radiation treatment are administered within a period of 12 weeks.

29. A method according to claim 1, wherein the radiation treatment is administered locally or to total skin.

30. A method according to claim 1, wherein the radiation treatment is administered to extracorporeal blood.

31. A method according to claim 1, wherein the radiation treatment is photopheresis.

32. A method according to claim 1, wherein the antibody, or antigen-binding fragment thereof, and radiation treatment are administered simultaneously.

33. A method of mediating radiation treatment of a CD4+ T-cell lymphoma comprising administering to a subject in need thereof a therapeutically effective amount of an antibody, or antigen-binding fragment thereof, comprising heavy and light chain variable region sequences as set forth in SEQ ID NOs: 1 and 2, respectively, and radiation treatment, wherein the radiation treatment is selected from the group consisting of psoralen and long-wave ultraviolet radiation (PUVA); UVB narrow band UVB; high dose UVA; electron beam; x-ray; and photopheresis, wherein the psoralen is a photosensitizer.

34. A method according to claim 33, wherein the radiation treatment is PUVA.

\* \* \* \* \*